(12) United States Patent
Kong

(10) Patent No.: US 10,975,148 B2
(45) Date of Patent: Apr. 13, 2021

(54) CHIMERIC ANTIGEN RECEPTORS, AND T CELLS IN WHICH CHIMERIC ANTIGEN RECEPTOR IS EXPRESSED

(71) Applicant: CellabMED Inc., Seoul (KR)

(72) Inventor: Seogkyoung Kong, Seoul (KR)

(73) Assignee: CELLABMED INC., Seoul (KR)

( * ) Notice: Subject to any disclaimer, the term of this patent is extended or adjusted under 35 U.S.C. 154(b) by 361 days.

(21) Appl. No.: 15/750,453

(22) PCT Filed: Aug. 5, 2016

(86) PCT No.: PCT/KR2016/008632
§ 371 (c)(1),
(2) Date: Feb. 5, 2018

(87) PCT Pub. No.: WO2017/023138
PCT Pub. Date: Feb. 9, 2017

(65) Prior Publication Data
US 2018/0265585 A1    Sep. 20, 2018

(30) Foreign Application Priority Data
Aug. 5, 2015  (KR) .................. 10-2015-0110788

(51) Int. Cl.
| | | |
|---|---|---|
| C12N 15/85 | (2006.01) | |
| C12N 15/62 | (2006.01) | |
| C07K 19/00 | (2006.01) | |
| A61K 35/17 | (2015.01) | |
| C07K 16/28 | (2006.01) | |
| C07K 16/24 | (2006.01) | |

(52) U.S. Cl.
CPC .......... *C07K 16/2818* (2013.01); *A61K 35/17* (2013.01); *C07K 16/24* (2013.01); *C07K 16/2809* (2013.01); *C07K 16/2875* (2013.01); *C07K 19/00* (2013.01); *C12N 15/62* (2013.01); *C12N 15/85* (2013.01); *C07K 2317/24* (2013.01)

(58) Field of Classification Search
CPC .................. C07K 14/5437; C07K 14/7051
See application file for complete search history.

(56) References Cited

U.S. PATENT DOCUMENTS

| | | | | |
|---|---|---|---|---|
| 9,650,428 B2 * | 5/2017 | Sampath | ............ | C07K 14/5437 |
| 9,914,909 B2 * | 3/2018 | Brown | ................. | C12N 5/0636 |
| 2014/0271582 A1 * | 9/2014 | Forman | .................. | A61P 35/02 |
| | | | | 424/93.21 |
| 2015/0139943 A1 | 5/2015 | Campana et al. | | |

FOREIGN PATENT DOCUMENTS

| | | | |
|---|---|---|---|
| BY | 4483 C1 | 3/1997 | |
| CA | 2195653 A1 | 2/1996 | |
| CN | 102775500 A | 11/2012 | |
| JP | 2012-501180 A | 1/2012 | |
| KR | 10-2013-0124521 | 11/2013 | ............. C12N 15/62 |
| WO | WO-2010/025177 A1 | 3/2010 | |
| WO | WO-2014/100385 A1 | 6/2014 | |
| WO | WO-2014/127261 A1 | 8/2014 | |
| WO | WO-2014/144622 A2 | 9/2014 | |
| WO | WO-2015/010096 A1 | 1/2015 | |
| WO | WO-2015/063069 A1 | 5/2015 | |
| WO | WO-2015/095895 A1 | 6/2015 | |
| WO | WO-2015/098112 A1 | 7/2015 | |

OTHER PUBLICATIONS

Thompson & Debinski, J Biol. Chem 274:29944-50 (Year: 1999).*
Nguyen et al., Neuro-Oncology 14(10): 1239-53 (Year: 2012).*
Nash et al., Crit. Rev. Oncol/Hematol 39:87-98 (Year: 2001).*
Krebs et al., Cytotherapy; 16:1121-31 (Year: 2014).*
Thaci et al., Neuro-Oncology 16(10):1304-12 (Year: 2014).*
Nguyen Phuong et al., Blood, 2003, vol. 102, No. 13, pp. 4320-4325.
Liu Daofeng et al., Clinical Immunology, 2013, vol. 149, No. 1, pp. 55-64.
Brian G. Till et al., Blood, 2012, vol. 119, No. 17, pp. 3940-3950.
Seogkyoung Kong et al., Clinical Cancer Research; 18(21) Nov. 1, 2012, pp. 5949-5960.
A. B. Madhankumar et al., Neoplasia, 2004, vol. 6, No. 1, pp. 15-22.
Brown, Christine E., et al. (2015) "Bioactivity and Safety of IL13Ra2-Redirected Chimeric Antigen Receptor CD8+T Cells in Patients with Recurrent Glioblastoma.", *Clin. Cancer Res.*, vol. 21, No. 18, pp. 4062-4072. (Sep. 15, 2015).
Dotti, Gianpietro, et al. (2014) "Design and development of therapies using chimeric antigen receptor-expressing T cells." *Immunol Rev*, 257(1):107-126.
Johnson, Laura A. et al. (2015) "Rational Development and Characterization of Humanized Anti-EGFR Variant iiI Chimeric Antigen Receptor T Cells for Glioblastoma", Science Translational Medicine, vol. 7, No. 275, 275ra22.

(Continued)

*Primary Examiner* — Jessica H Roark
(74) *Attorney, Agent, or Firm* — Harness, Dickey & Pierce, P.L.C.

(57) ABSTRACT

Disclosed is a chimeric antigen receptor comprising an antigen binding domain; a hinge region; a transmembrane domain; a costimulatory domain; and a cytoplasmic signaling domain.

20 Claims, 16 Drawing Sheets
Specification includes a Sequence Listing.

(56) References Cited

OTHER PUBLICATIONS

Kalos, Michael, et al. (2011) "T Cells with Chimeric Antigen Receptors Have Potent Antitumor Effects and Can Establish Memory in Patients with Advanced Leukemia." Science Translational Medicine, 3(95):95ra73. (Aug 10, 2011).
Kowolik, Claudia M., et al. (2006) "CD28 Costimulation Provided through a CD19-Specific Antigen Receptor Enhances In vivo Persistence and Antitumor Efficacy of Adoptively Transferred T Cells.", Cancer Research, vol. 66, No. 22, pp. 10995-11004. (Nov. 15, 2006).
Maude, M.D., Shannon L., et al. (2014) "Chimeric Antigen Receptor T Cells for Sustained Remissions in Leukemia.", N. Engl. J. Med., 371;1507-1517. (Oct. 16, 2014).
Porter, David L., et al. (2011) "Chimeric Antigen Receptor—Modified T Cells in Chronic Lymphoid Leukemia.", N. Engl. J. Med., 365:725-733. (Aug. 25, 2011).
International Search Report from corresponding International Application No. PCT/KR2016/008632, dated Nov. 21, 2016, and its English translation.
Written Opinion from corresponding International Application No. PCT/KR2016/008632, dated Nov. 21, 2016.

\* cited by examiner

US 10,975,148 B2

CHIMERIC ANTIGEN RECEPTORS, AND T CELLS IN WHICH CHIMERIC ANTIGEN RECEPTOR IS EXPRESSED

CROSS-REFERENCE TO RELATED APPLICATIONS

This application is a national phase application of PCT Application No. PCT/KR2016/008632, filed on 5 Aug. 2016, which claims benefit of Korean Patent Application 10-2015-0110788, filed on 5 Aug. 2015. The entire disclosure of the applications identified in this paragraph are incorporated herein by reference.

TECHNICAL FIELD

The present invention relates to a chimeric antigen receptor recognizing a cancer cell surface antigen, and a T cell in which the receptor is expressed. Specifically, the present invention relates to a chimeric antigen receptor with an excellent expression rate, and a T cell in which the receptor is expressed. More specifically, the present invention relates to a chimeric antigen receptor and a T cell in which the receptor is expressed, said chimeric antigen receptor comprising a cancer cell surface antigen binding domain; a hinge region; a transmembrane domain; a costimulatory domain; and a cytoplasmic signaling domain, characterized in that the costimulatory domain consists of mutated CD28 or TNFRSF9. Additionally, the present invention relates to a chimeric antigen receptor and a T cell in which the receptor is expressed, characterized in that the antigen binding domain binds to an antigen selected from the group consisting of IL13Rα2, an antigen associated with an angiogenic activity, EGFRvIII, EphA2, αVβ3, and glypican 1.

In addition, the present invention relates to the chimeric antigen receptor and the T cell in which the receptor is expressed, characterized in that three glycines are additionally introduced between the antigen binding domain and the hinge region.

Further, the present invention relates to the chimeric antigen receptor and the T cell in which the receptor is expressed, characterized in that the cytoplasmic signaling domain uses a CD3ζ signaling domain of a normal person where extra Glutamine is comprised, not a CD3ζ signaling domain of a Jurkat T cell.

Moreover, the present invention relates to the chimeric antigen receptor and the T cell in which the receptor is expressed, the chimeric antigen receptor comprising any one of the predetermined antigen binding domain, the costimulatory domain and the cytoplasmic signaling domain described above, or all of them.

BACKGROUND ART

T cells (hereinafter, in the present specification, this is sometimes referred to as "CAR-T cells") expressing chimeric antigen receptors (hereinafter, in the present specification, this is sometimes referred to as "CARs") mean recombinant T cells in which a gene coding a receptor recognizing a cancer cell surface antigen specifically expressed on the surface of the cancer cell is introduced into the T cell to kill the cancer cell. Dr, Zelig Fshhar, et. al., who is a chemist and an immunologist of the Weizmann Institute of Science in Israel, had succeeded in making T cells provided with chimeric antigen receptors, by obtaining a theory that when T cells with a receptor binding to an antigen specifically expressed in a cancer call is artificially made, an immune response occurs, targeting only to the cancer cell, so as to kill the cancer cell, and then reported this fact in PNAS in 1989.

However, CAR-T cells produced in the early stage, i.e. the 1st generation CAR-T cells used only CD3ζ as a signaling domain, but its therapeutic effect was insignificant, and also, there was a disadvantage that the duration time was short. Thus, efforts have been made to improve the reactivity of the CAR-T cells, and as a result, 2nd generation CAR-T cells in which a costimulatory domain (CD28 or CD137/4-1BB) and CD3ζ are combined were produced, wherein the number of CAR-T cells present in the body was significantly increased as compared to the number of the 1st generation CAR-T cells. Meanwhile, the 2nd CAR-T cells used one type of the costimulatory domain, and CAR-T cells using two types of the costimulatory domain are referred to 3rd generation CAR-Ts. Most of the recent studies focus on the 2nd generation and 3rd generation CAR-T cells. Meanwhile, regarding methods for treating cancers using the CAR-T cells, there was a report that when cytotoxic T cells transformed to recognize CD19 were injected into three patients with end-stage chronic lymphoid leukemia (CCL), leukemia was completely treated in two of the patients, and the condition was continued for about 10 months (N. Engl J Med 2011; 365:725-733 Aug. 25, 2011, Sic. Transl. Med 2011 Aug. 10; 3(95):95ra73). The CAR-Ts used herein correspond to the 2nd generation, and use 4-1BB as the costimulatory domain and CD3ζ as the signaling domain. The antigen binding domain of the CAR-T cells recognizes CD19, which is found on the surface of the leukemia cancer cells, as an antigen.

In addition, there was a report that when patients with acute leukemia were treated by administering CTL019, 27 of the 30 patients had experienced complete remission, 67% of all patients experienced complete remission for 2 years, and 78% of the patients were survived for 2 years. Given that the subject patients were relapsing or refractory patients, this result was very surprising (N Engl j Me-d 2014; 371:1507-1517, Oct. 16, 2014).

At present, for therapeutic methods using various CAR-T cells, clinical tests on various hematologic cancers such as lymphoma, myeloma, etc. have been conducted, and it is expected that CAR-T will become available as an available medicine in the market. Since cancer treatment using CAR-T cells is a self-derived method, this product could not be mass-produced; however, this is patient-specific treatment, so its therapeutic effect is incomparably higher than the existing anticancer drugs.

PATENT LITERATURE

Korean Patent Laid-Open No. 10-2013-0124521

Non-Patent Literature

Immunol Rev, 2014, 257(1):107-126
N Engl J Med 2014; 371: 1507-1517, Oct. 16, 2014
Science Translational Medicine 18 Feb. 2015: Vol. 7, Issue 275, pp. 275ra22

DETAILED DESCRIPTION

Technical Task

The present invention has a task for providing CAR and CAR-T cells with significantly excellent expression rates and therapeutic effects as compared to the conventionally known CAR-T cells. More specifically, the present invention has a task for providing, in the 2nd generation and 3rd generation CAR-T cells, a costimulatory domain capable of being introduced into various CAR-T cells, as the costimulatory domain serving a main role in the function. Furthermore, the present invention has a task for providing various antigen binding domains capable of binding to an antigen expressed on the surface of a specific cancer cell and also capable of forming CAR-T cells. In addition, the present invention has a task for providing a method for improving the expression rates of various CAR-T cells and the therapeutic effects thereof, with a chimeric antigen receptor characterized by having further amino acid sequences that can be additionally introduced between the antigen binding domain and the hinge domain.

Means for Achieving the Technical Task

As means for achieving the aforementioned tasks, the present invention describes the following technical idea.

Disclosed is a chimeric antigen receptor and a CAR-T cell in which the receptor is expressed, the chimeric antigen receptor comprising an antigen binding domain; a hinge region; a transmembrane domain; a costimulatory domain; and a cytoplasmic signaling domain, characterized by independent comprising a specific costimulatory domain, or a specific antigen binding domain, and a specific amino acid sequence added between the antigen binding domain and the hinge domain, or in that the cytoplasmic signaling domain uses a CD3ζ signaling domain of a normal person where extra Glutamine is comprised, not a CD3ζ signaling domain of a Jurkat T cell, or by comprising a combination thereof.

Effect of the Invention

The CAR-T cell comprising the antigen binding domain; or the costimulatory domain; or the signaling domain described in the present invention has the effect that the therapeutic efficacy and expression rate are significantly excellent.

BRIEF DESCRIPTION OF THE DRAWINGS

The current embodiments are illustrated in the drawings for the purpose of exemplifying the present invention. However, it should be noted that the present invention is not limited to the accurate arrangements and methods of the embodiments illustrated in the drawings.

FIG. 12 shows the production of anti-angiogenic CAR. Successful anti-cancer CAR therapies require not only antigen-specific CAR–T cells but also accessing CAR–T cells to cancer cells and maintaining CAR–T cell function in the immunosuppressive tumor microenvironment. Therefore, anti-angiogenic CAR was produced.

BEST MODE

Figure 1:
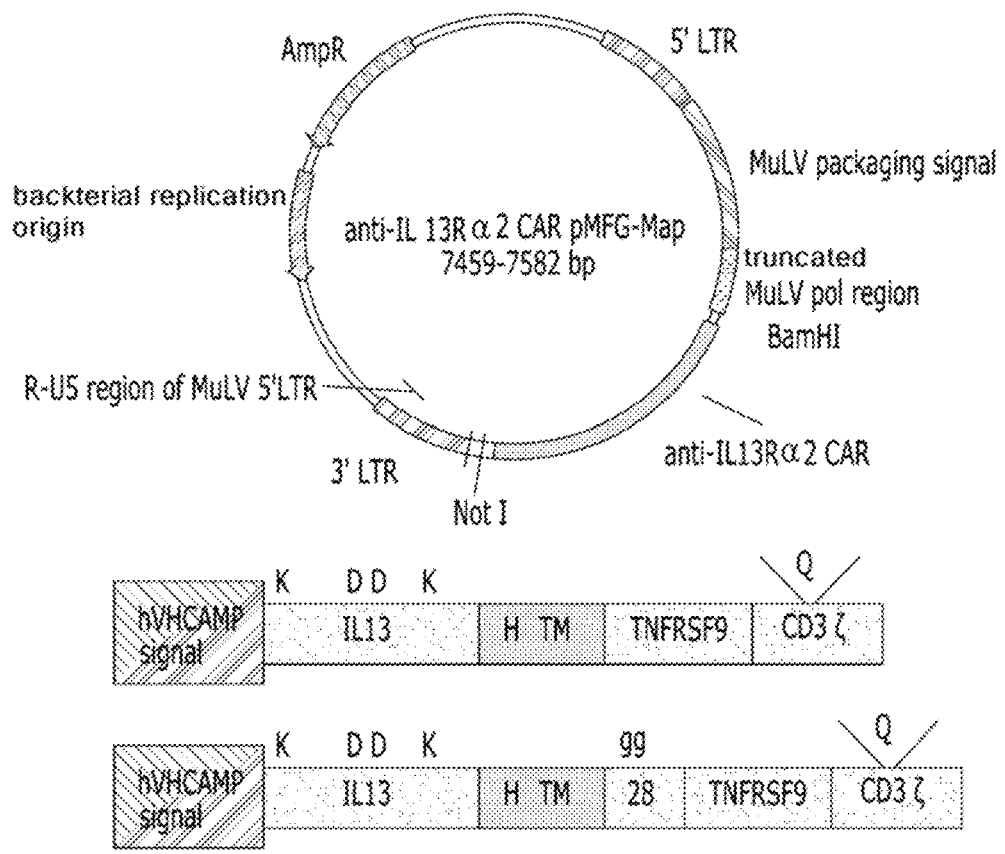
FIG. 1 illustrates a retrovirus vector and transgene representing the main functional elements of one embodiment of the CAR-T cell described in the present invention. Specifically, this figure illustrates a clinical-grade retrovirus vector indicating the expressions of mutated IL13 (E11K.R64D.S67D.R107K), human CD8α hinge and human CD8/human CD3 transmembrane domain in order to impart higher antigen affinity than two amino acid substituents (Glu-11, Arg-107) of IL13, and mutant human CD28 (RLLH→RGGH), human TNFRSF9, and CD3 zeta signaling domain of healthy person in order to increase the CAR expression rate. This figure is not illustrated in a constant accumulation.

The CAR–T cell according to the present invention is a recombinant T cell in which a receptor gene recognizing a cancer cell as an antigen is introduced, wherein the T cell consists of an antigen binding domain recognizing the antigen; a hinge region (or spacer) connecting the antigen binding domain and a transmembrane domain; the transmembrane domain; a costimulatory domain; and a cytoplasmic signaling domain.

The antigen binding domain, which is a site where a main signal is delivered and is present outside of a cell membrane, recognizes a cancer cell expressing a particular antigen. Thus, in the cancer treatment using CAR–T cell, the detailed treatment subject is determined by the antigen binding domain. The present invention describes, for example, a chimeric antigen receptor capable of specifically binding to IL13Rα2 overexpressed in glioblastoma, but the antigen binding domain is not specifically limited thereto. Glioblastoma (GMB) or glioblastoma multiforme is one of the most general brain tumors, which occupies about 12 to 15% of the brain tumors, and this is a general malignant brain cancer. Since this cancer is relatively rare as compared to a colorectal cancer or lung cancer, the studies on the treatment method thereof have not been actively conducted. The cells of glioblastoma are similar to astrocyte, but astrocyte serves as maintaining nerve cells and giving nutrition to nerves and a defense reaction to the damage of brain tissues. It is believed that genomic abnormality of stem cells or immature astrocyte is involved in occurrence and malignization of glioblastoma. For the treatment of glioblastoma, surgery, radiotherapy and chemotherapy are used. As chemotherapy, temozolomide, lomustine and carmustine, etc. are used, and recently, clinical tests such as tumor vaccine treatment and molecular targeted treatment have been conducted. However, there are still no useful therapeutic agents for the treatment of glioblastoma, and particular, although there was an attempt on the treatment of glioblastoma overexpressing IL13Rα2 using CAR–T cells using mutant IL13 where the 11th position is substituted with E11Y, Baylor college of medicine group reported that the therapeutic effect using the CAR–T cells using mutant IL13 where the 11th position is substituted with E11Y was not good in vivo. However, the CAR–T cell described in the present invention exhibits the excellent therapeutic effect of glioblastoma.

Sequence of the antigen binding domain binding to IL13Rα2 is identical to SEQ ID NO. 1, and in particular, mutant IL13 where the 11th, 64th, 67th and 107th positions are substituted with E11K.R64D.S67D.R107K, respectively, is newly described in the present invention. It should be noted, however, that the amino acids substituted in the corresponding positions can be replaced with amino acids having the similar property with the specific amino acids. Thus, the amino acids can be replaced with arginine (R) or histidine (H), instead of lysine (K), in the 11th position; with glutamic acid (E), instead of aspartic acid (D), in the 64th and 67th positions; and histidine (H), instead of lysine (K), in the 107th position.

IL13(E11K.R64D.S67D.R107K) where the four positions are mutated, described in the present invention, and analogue substituted with an amino acid having the same property in the same position have improved antigen affinity.

The antigen binding domain of the present invention can be produced so as to bind to an antigen expressed in various cancer cells as well as IL13Rα2 overexpressed in glioblastoma. For example, an antigen binding domain (SEQ ID NO. 2) capable of binding to an antigen associated with an angiogenic activity; an antigen binding domain (SEQ ID NO. 3) binding to EGFRvIII which is a main tumor antigen of glioblastoma and lung cancer, etc.; an antigen binding domain (SEQ ID NO. 4) binding to EphA2 which is a tumor antigen of glioblastoma, breast cancer, prostate cancer, etc.; an antigen binding domain (SEQ ID NO. 5) binding to αVβ3 which is a resistant marker of carcinoma stemness and receptor tyrosine kinase inhibitors (RTKIs) such as erlotinib of pancreatic cancer, lung cancer and breast cancer; an antigen binding domain (SEQ ID NO. 6) binding to glypican 1 overexpressed in pancreatic cancer, glioblastoma, breast cancer, etc. are described in the present invention. FIGS. 12 to 16 show the five kinds of CAR production comprising the above antigen binding domains. The respective figures illustrates the retrovirus vector and transgene representing the main functional element and shows the result of analyzing transformed cells checking on the cell surface expression of Anti-Angiogenic CAR using a Flow cytometry analysis.

The further characteristic of the present invention lies in additionally introducing three glycines between the antigen binding domain and the hinge region, in order to increase the solubility of a CAR protein to increase the expression of the chimeric antigen receptor. According to the study of the present inventors, the difference in solubility between the receptor in which three glycine between the antigen binding domain and the hinge region are introduced and the receptor in which three glycine are not introduced showed about 10 times, and this difference leads to a great difference in expression rate with regard to the production of CAR–T cells, and the difference of the expression rate is eventually directly connected to the therapeutic effect. For this reason, this can be deemed to be very advanced technical development. In addition, said three glycine (G) may be substituted with alanine (A), valine (V), leucine (L) or isoleucine (I), which are amino acids having the similar property.

Yet another characteristic of the present invention lies in the use of a specific costimulatory domain. In the CAR–T cells, when an antigen binding domain and an antigen bind to each other, the signal activates a T cell immune response through the cytoplasmic signaling domain (CD3ζ). The costimulatory domain, which is a site where a costimulatory signal is delivered, serves a role in delivering a signal such that the CAR–T cell recognizing a specific antigen binding to the antigen binding domain causes an immune response to help proliferation and persistence in the body longer. Meanwhile, such costimulatory domain is a component which was not present in the first generation CAR-T cell, and the 2nd CAR-T cell uses one costimulatory domain, and the 3rd generation CAR-T cell uses two costimulatory domains. The CAR-T cell improves proliferation and persistence in the body longer. in the costimulatory domain inside the cells over the generations such as 1st generation, 2nd generation, 3rd generation, etc., and thus the cells have been developed in re-combination with genes such that many CAR-T cells against the cancer cell are made in the body even after injecting a small number of cells, and the cells can last in the body for a long time even after injection. That is, in the case of the first generation, there was a limitation of signaling because it comprises only CD3ζ without the costimulatory domain, but in the 2nd and 3rd generations, 4-1BB or OX40, etc. is additionally introduced so as to improve proliferation and persistence in the body longer.

In addition, the present inventors used the costimulatory domain which generates a mutant in the predetermined position of CD28 such that by the improvement of the expression rate of CAR-T cells, the therapeutic effect can be exhibited even if less CAR-T cells are used, and furthermore, the inventors have found that by using two costimulatory domains in which mutated CD28 and TNFRSF9 are combined, 'proliferation and persistence in the body' is improved, resulting in the increased therapeutic efficacy.

Accordingly, the further technical characteristic of the present invention lies in a chimeric antigen receptor and a CAR-T cell in which the receptor is expressed, the chimeric antigen receptor consisting of an antigen binding domain; a transmembrane domain; a costimulatory domain and a cytoplasmic signaling domain, wherein the costimulatory domain comprises CD28 or TNFRSF9, or CD28 and TNFRSF9. Here, CD28 may comprise a mutant amino acids in the $6^{th}$ to $9^{th}$ positions of (SEQ ID NO. 7 are substituted from RLLH to RGGH) for increasing the expression of the chimeric antigen receptor. Amino acid sequences of the wild type of CD28 and TNFRSF9, which may be comprised as the costimulatory domain of the present invention, are indicated with Sequence Nos. 7 and 8. In addition, in the mutated CD28 (SEQ ID NO. 27 wherein the amino acids in the 6th to 9th positions of SEQ ID NO. 7 are substituted from RLLH to RGGH), the substituted amino acid is glycine (G), but this can be replaced with amino acid similar thereto, for example alanine (A), valine (V), leucine (L) or isoleucine (I). The hinge region of the present invention is a portion connecting the antigen binding domain and the transmembrane domain, and this is also called spacer. The hinge region has the purpose for expanding the antigen binding domain from T cell membrane. As the hinge region of the present invention, a hinge region typically used in the pertinent technical field can be used, and for example, the hinge region can be derived from CD8 hinge region (SEQ ID NO. 9, SEQ ID NO. 10). As aforementioned, another technical characteristic of the present invention lies in three glycines additionally introduced between the antigen binding domain and the hinge region.

The transmembrane domain of the present invention severs a role as an anker of CAR molecular and at the same time a role in delivering a signal received from the antigen binding domain to the costimulatory domain and the cytoplasmic signaling domain. The transmembrane domain is not limited to the transmembrane domain of the present invention, and typical transmembrane domains used for the CAR production can be used, and for example, human CD8/CD3 transmembrane domain can be used (SEQ ID NO. 11, SEQ ID NO. 12).

As the cytoplasmic signaling domain of the present invention, a CD3ζ signaling domain of a normal person where extra Glutamine is comprised, not a CD3ζ signaling domain of a Jurkat T cell, was used, and the extra glutamine means glutamine (Q) in the 50th position in SEQ ID NO. 13.

The technical idea of the present invention includes the use of the aforementioned technical characteristics alone and the use of the combination thereof. That is, the implementation of the technical characteristics of the present invention includes all of the CAR-T cells comprising the predetermined antigen binding site described in the present invention; the CAR-T cells in which three glycine are additionally introduced between the antigen binding domain and the hinge region; and the CAR-T cells comprising the costimulatory domain described in the present invention.

The nucleic acid sequences of polypeptide constituting the domains described in the present specification can be obtained using the recombinant methods known in the pertinent technical field, and for example, can be obtained by screening library from cells expressing the gene using the standard technique, or inducing a gene from a known vector to comprise the same gene, or directly isolating from cells or tissues comprising the same gene. Alternatively, the interested gene can be generated by synthesis, not cloning.

The method for introducing and expressing a gene into cells has been known in the pertinent technical field. The expression vector can be rapidly introduced into host cells by any method known in the pertinent technical field. For example, in the present invention, the CAR-T cells can be produced by joining a CAR gene fragment finally produced to an MFG retrovirus expression vector cleaved with XhoI/NotI. It should be understood that the present invention comprises any various mutants for each of the components of the structure.

Cancers to be treated may include non-solid tumors (for example, hematological tumors, e.g. leukemia and lymphoma) as well as glioblastoma, or may include solid tumors.

As such, it takes several steps to produce recombinant CAR-T cells and inject the cells into cancer patients. T cells are isolated from the blood of patients, and then DNA designed with CAR is introduced into the T cells using an expression vector, and the CAR-T cells are proliferated, and then injected back into the patient.

MODE FOR CARRYING OUT THE INVENTION

Hereinafter, the present invention is specified through the examples. Please be noted, however, that the following examples are not intended to limit the technical scope of the present invention in any meaning.

Figure 2:
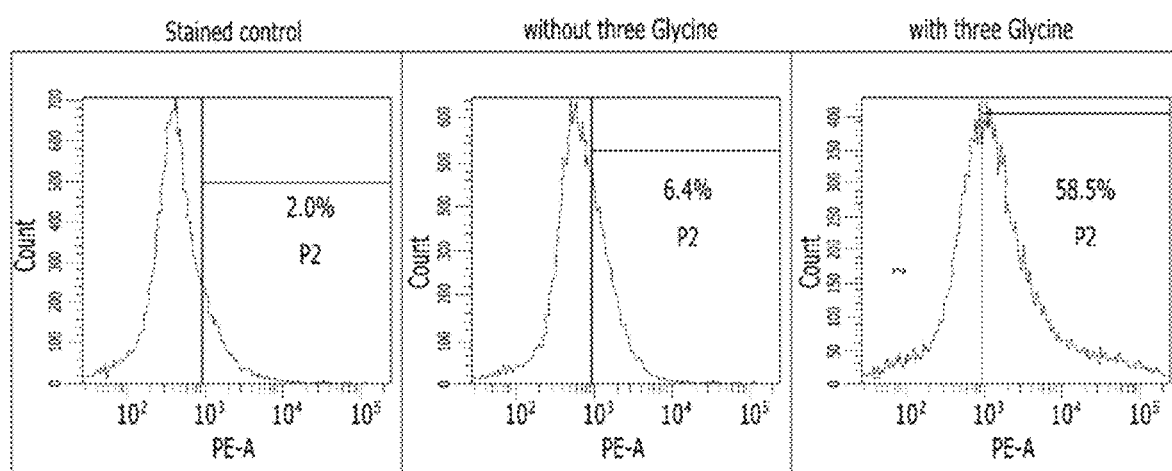
FIG. 2 shows that the expression rate is increased after adding three glycines between the antigen binding domain and the hinge region, in order to increase the solubility of a CAR protein so as to increase the expression of the chimeric antigen receptor.
Figure 3:
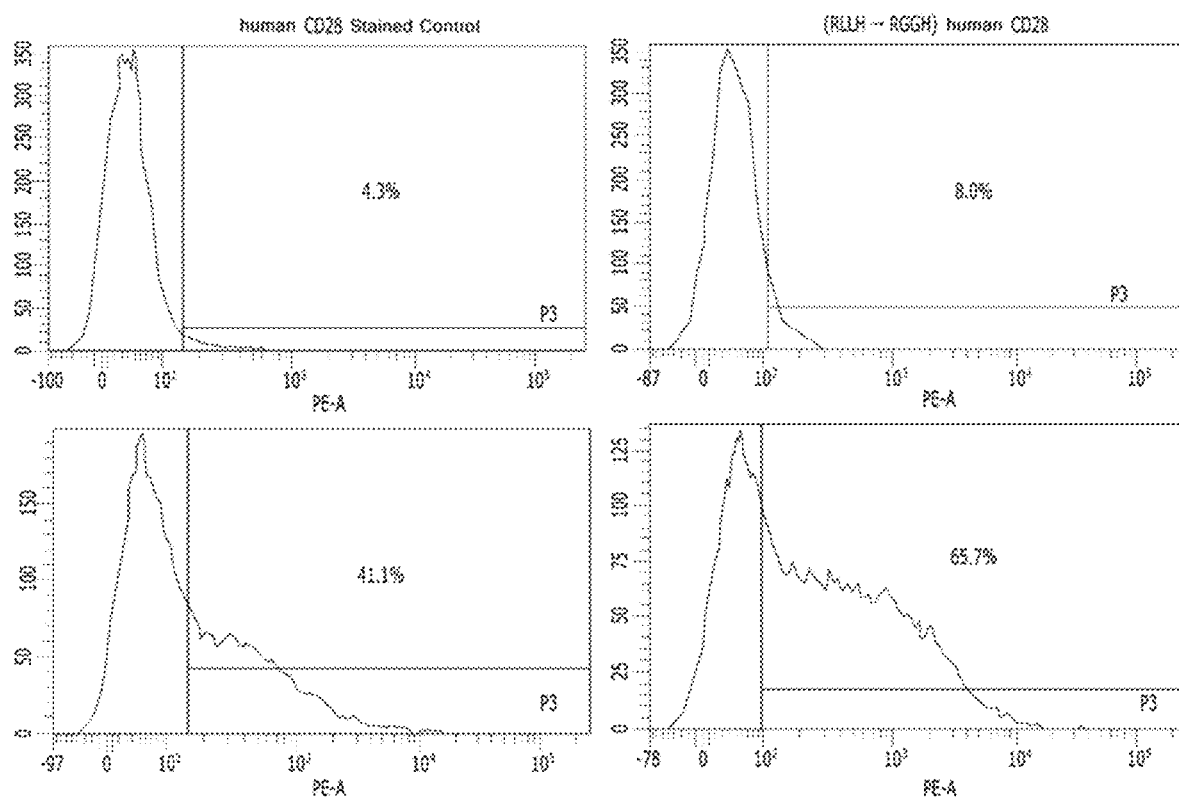
FIG. 3 shows that the expression rate is increased when using mutant (RLLH→RGGH) of human CD28, in order to increase the expression of the chimeric antigen receptor of the CAR protein.

Example 1: Construction of an Expression Vector Having 2nd Generation (YYB-103, IL13.E11K.R64D.S67D.R107K.TNFRSF9.CD3ζ) and 3rd Generation (YYB-103A, IL13.E11K.R64D.S67D.R107K.TNFRSF9.CD3ζ) Chimeric Antigen Receptors Specifically Binding to IL13Rα2 Overexpressed in Cancer Cell The present inventor produced mutant IL13 (E11K.R64D.S67D.R107K) in order to impart a higher antigen affinity than two amino acid substitutions (Glu-11, Arg-107) of IL13, and produced chimeric antigen receptors comprising one co-stimulation domain (TNFRSF9) and two co-stimulation domains (CD28, TNFRSF9) of the cytoplasmic signaling domain of CAR-T cell (FIG. 1). In the present invention, three glycines were added between the antigen binding domain and the hinge region in order to increase the solubility of a CAR protein to increase the expression of the chimeric antigen receptor (FIG. 2). The CD28 cytoplasmic signaling domain used in the present invention comprises mutant (RLLH→RGGH) human CD28 DNA sequences for increasing the solubility of a CAR protein to increase the expression of the chimeric antigen receptor (FIG. 3). Human CD3ζ signaling domain of healthy normal person, not a CD3ζ signaling domain of a Jurkat T cell, was used. Human IL13(P35225.1), human CD3(P20963-1), human CD8a (P01732), human CD28(P10747), human TNFRSF9 (Q07011), and human kappa light chain signal sequence (HuVHCAMP) were optimized using science literatures and publicly available database, the 2nd and 3rd generation chimeric antigen receptors (YYB-103, IL13.E11K.R64D.S67D.R107K.TNFRSF9.CD3 and YYB-103A, IL13.E11K.R64D.S67D.R107K.28.TNFRSF9.CD3ζ) consisting of codon-optimized synthetic DNA was produced (FIG. 1). The completed structure comprises kozak consensus ribosome-binding sequence, human kappa light chain signal sequence (HuVHCAMP), human IL13.E11K.R64D.S67D.R107K mature protein sequence (human IL13 (E11K.R64D.S67D.R107K)), an addition of three glycine (GGG) between the antigen binding domain and the hinge region in order to increase the solubility of a CAR protein to increase the expression of the chimeric antigen receptor (FIG. 2), the hinge region of human CD8a, human CD8/CD3 transmembrane domain, the costimulatory domain of cytosol CD28 transformed to mutant (RLLH→RGGH), the costimulatory domain of cytosol TNFRSF9, CD3ζ cytoplasmic signaling domain of healthy person and XhoI/NotI cleavage portion. The entire sequences of YYB-103 and YYB-103A are represented in Sequence Nos. 14 and 15. A CAR gene fragment finally produced was joined to an MFG retrovirus expression vector cleaved with XhoI/NotI (Emtage PC, etc., Clin Cancer Res, 2008 14L8112-8122) (FIG. 1). In the present example, in order to compare the activity of chimeric antigen receptors, two amino acid substitutions (Glu-11, Arg-107), 3rd generation chimeric antigen receptors (YYB-103B, IL13 (E11K.R107K).28.TNFRSF9.CD30 of IL13 was additionally produced (SEQ ID NO. 16).

Figure 4:
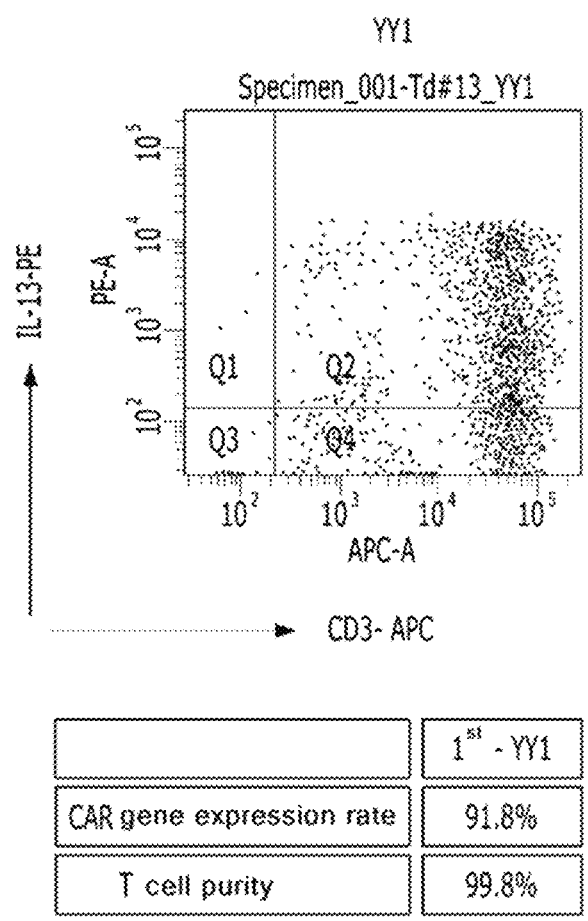
FIG. 4 shows the result of analyzing transformed T cell using a Flow cytometry analysis, in order to verify the purity of CAR-T cell and the expression rate of CAR produced by a production process set for clinical test. This figure shows the CAR expression rate and the T cell purity.

Example 2: Production of T Cells Transformed to 2nd Generation (YYB-103, IL13.E11K.R64D.S67D.R107K.TNFRSF9.CD3ζ) and 3rd Generation (YYB-103A, IL13.E11K.R64D.S67D.R107K.28.TNFRSF9.CD3ζ) Chimeric Antigen Receptors Specifically Binding to IL13Rα2 Overexpressed in Cancer Cells PG13 clone with high titer, expressing CAR, was produced by temporarily infecting phoenix-empo and phoenix-eco cells with the retrovirus expression vector YYB-103 or YYB-103A produced in Example 1, and subsequently transduced PG13 cells with acellular vector stock from the infected phoenix-empo and phoenix-eco cells. Single clone with high titer was obtained by a flow cytometer after staining PG13/YYB-103 cells using an anti-iL-13 monoclonal antibody (BD Pharmingene). PG13/YYB-103 single clone with high titer was produced by the second subcloning according to the limit dilution assay. Subclone PG13/YYB-103-13 showed the stably high CAR expression, and was selected to transduce peripheral blood mononuclear cells (PBMC) of human. The transduction efficiency of the PBMC/YYB-103-13 checked with anti-iL-13 monoclonal antibody (BD Pharmingen) using a flow cytometry analysis. The supernatant of PG13/YYB-103-13 cells comprises retrovirus and collected for the genetic modification of PBMC. PBMC were separated using centrifugation by putting whole blood obtained from a healthy human donor into Ficoll Paque (GE Healthcare). The separated PBMC was cultured by adding anti-CD3 monoclonal antibody (eBioscience) 100 ng/mL under the condition of Human IL-2 (NOVARTIS) 100 IU/mL to activate the T cell fraction (BL Levine, Cancer Gene Therapy, 2015, 22:79-84). After 2 to 3 days activation, most of the cells were T cells, and comprised natural killer cells at a ratio of 0-2%. After 2 to 3 days activation step, the T cells were subject to transduction two times over 2 days using retroviral supernatant and were washed, and then the cells were proliferated for 4 to 7 days in a flask. The cells were cultured in a stirring platform device (WAVE bioreactor system) for 12 to 14 days. IL-2 was maintained in the amount of 100 IU/mL. The CAR–T cell modified in such manner was used for the analysis experiment (FIG. 4).

Experimental Example 1: Check for the CAR Expression Rate of the T Cell Surface Transformed to a Chimeric Antigen Receptor Experimental Method (Flow Cytometric Analysis)

For flow cytometry (>30,000 events), BD LSRII equipment (Becton Dickinson) and BD FACSDiva software (Becton Dickinson) were used. Specifically, before adding a PE-conjugated anti-human IL-13 monoclonal antibody (BD Pharmingen), the cell was washed once with PBS containing 2% bovine serum albumin. After washing, the cell was reacted with the respective antibodies for 30 minutes at 4° C. in the state where light was blocked and then washed once, and thereafter, the expression rate of the transduced T cell surface CAR was checked. In addition, in order to verify the cell surface expression of IL13Rα2 and IL13Rα1, anti-human IL13Rα antibody (R&D systems), donkey anti-goat IgG phycoerythrin secondary antibody (R&D systems), and anti-human IL13Rα phycoerythrin (R&D systems) were used, and as a control, isotype antibody was comprised.

Experimental Result

In order to verify that IL13Rα2-specific CAR(YYB-103, IL13.E11K.R107K.TNFRSF9.CD3ζ; YYB-103A, IL13.E11K.R64D.S67D.R107K.28.TNFRSF9.CD3ζ; YYB-103B, IL13.E11K.R107K.28.TNFRSF9.CD3ζ) produced in Example 1 was expressed on the T cell surface, T cell cultivation was carried out for 12-14 days according to Example 2 and then the flow cytometric analysis was carried out according to the experimental method. As the result of the analysis, the expression rates of the chimeric antigen receptors expressed on the living T cell surface were 90.5% to 92.8% in the seven (7) blood donors. When the cultivation was maintained, the expression of IL13Rα2-specific chimeric antigen receptor was stably maintained for 4 weeks, without additional T cell activation or transduction. In addition, in the cultured cell, the ratios of entire T cell, CD4 T cell, CD8 T cell, B cell, and Monocyte were analyzed. As the result, it was confirmed that B cell existed in the amount of 0.5-1.2%, and no Monocyte exists.

Example 3: Measurement of Cytotoxicity and IFN-γ Secretion of the T Cell Transformed to 2nd Generation (YYB-103, IL13.E11K.R64D.S67D.R107K.TNFRSF9.CD3ζ) and 3rd Generation (YYB-103A, IL13.E11K.R64D.S67D.R107K.TNFRSF9.CD30 Chimeric Antigen Receptors Specifically Binding to IL13Rα2 Overexpressed in Cancer Cell IL13Rα2-specific cytotoxicity and IFN-γ secretion were measured using the CAR-T cell produced in Example 2. In order to measure IL13Rα2-specific cytotoxicity and IFN-γ secretion, U251 that is a glioblastoma human cell line overexpressing IL13Rα2, and primary HUVEC that does not express IL13Rα2, as a normal cell control, were used.

Experimental Example 1: Cytotoxicity Check for Glioblastoma Overexpressing IL13Rα2

Experimental Method

In order to measure cytotoxicity of IL13Rα2-specific CAR-T cell effector (IL13Rα2-specific CAR+ T cell effector), cytotoxicity assay was carried out using a DELFIA (Perkin Elmer) kit. Specifically, CAR-T cell effector cells were used 12 to 14 days after the cell activation to anti-CD3, and the experiment was carried out three times under the condition where the effector cell was put in a 96 well plate in which IL13Rα2 target cell existed at a ratio of 5:1 (effector:target) and a ratio of 0.625:1 (effector:target) and reacted for 2 hours at 37° C. In the 96 well plate used in this analysis experiment, 5,000 target cells were added per well, and U251, which is a glioblastoma cell line overexpressing IL13Rα2, was used as the used target cell, and primary HUVEC was used as a normal cell control.

Experimental Result

Figure 5:
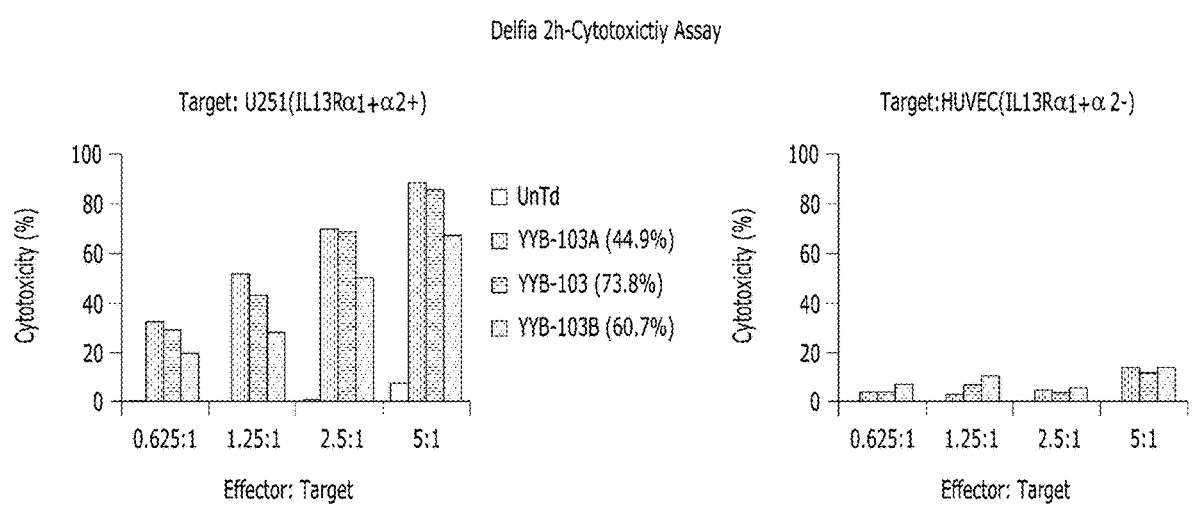
FIG. 5 shows the comparison of cytotoxicity of T-cells, in which IL13 (Glu-11, Arg-107) where two positions are substituted, and IL13(IL13.E11K.R64D.S67D.R107K) where four positions are substituted are introduced.

It was analyzed whether the target cancer cell (U251) overexpressing IL13Rα2 was effectively killed by IL13Rα2-specific CAR(YYB-103, IL13.E11K.R64D.S67D.R107K.TNFRSF9.CD3ζ; YYB-103A, IL13.E11K.R64D.S67D.R107K.28.TNFRSF9.CD3ζ; YYB-103B, IL13.E11K.R107K.28.TNFRSF9.CD3ζ) T cells produced according to the present invention. As the experimental method, the method of comparing and analyzing cytotoxicity by culturing the target cancer cell (U251) and the normal cell (HuVEC) aforementioned together with the respective activated CAR-T cell was used. As illustrated in FIG. 5, in all cases, the result was obtained that when CAR specific to IL13Rα2 was expressed, the CAR expression induced the killing of glioblastoma U251 cell expressing IL13Rα2 at a high level, as compared to the activated T cell that was not transduced (FIG. 5). Specifically, in the case of the T cell expressing YYB-103 (IL13.E11K.R64D.S67D.R107K.TNFRSF9.CD3ζ), YYB-103A(IL13.E11K.R64D.S67D.R107K.TNFRSF9.CD3ζ), and YYB-103B(IL13.E11K.R107K.28TNFRSF9.CD3ζ) CAR produced in Example 2 of the present invention, as the E:T ratio increased, cytotoxicity gradually increased; however, in the case of T cell that did not express CAR, cytotoxicity rarely increased. In addition, as the result of comparing YYB-103B (IL13.E11K.R107K.28.TNFRSF9.CD3ζ) CAR, in which two amino acids of IL13 were substituted, and YYB-103 (IL13.E11K.R64D.S67D.R107K.TNFRSF9.CD30 and YYB-103A (IL13.E11K.R64D.S67D.R107K.28.TNFRSF9.CD30, in which four amino acids of IL13 were substituted, which were used in order to impart higher antigen affinity, in the case of YYB-103B in which only two amino acids were substituted, 67.4% of cytotoxicity was shown at the E:T ratio of 5:1, but when YYB-103 and YYB-103A in which mutant IL13.E11K.R64D.S67D.R107K in which four amino acids of IL13 were substituted were used, 85.6% and 87.7% of cytotoxicity were shown, respectively. This shows that cytotoxicity of T-cell in which mutant IL13.E11K.R64D.S67D.R107K in which four amino acids of IL13 were substituted was introduced is superior in both 2nd generation and 3rd generation as compared to cytotoxicity of T-cell in which mutant IL13.E11K.R107K in which two amino acids of IL13 were substituted was introduced.

From the experimental result of using, as a normal cell control, HUVEC cell which does not express IL13Rα2 but minimally expresses IL13Rα1, as an object to be compared with the target cells, it was confirmed that the CAR-T cell (12.3-14% cytotoxicity) specific to IL13Rα2 has very weak cytotoxicity (FIG. 5). This shows that due to the property of the HUVEC cell which expresses IL13Rα1 and does not express IL13Rα2, the chimeric antigen receptor used in the experiment specifically binds to IL13Rα2. Through the present experimental example, it was demonstrated that IL13Rα2-specific chimeric antigen receptor T cell does not exhibit toxicity to a normal cell (HUVEC) and can significantly kill the target cancer cell (U251) expressing IL13Rα2.

Experimental Example 2: Measurement of Anticancer Activity Change According to CAR Expression Rate Experimental Method In order to measure the anticancer activity change according to the expression rate of IL13Rα2-specific CAR, the cytotoxicity analysis was carried out. Specifically, 2nd Generation IL13.E11K.R64D.S67D.R107K.TNFSFR9.CD3ζ, which is YYB-103, was used as an effector cell for CAR-T cell, and U251 cell line overexpressing IL13Rα2 was used as a Target cell. For the cytotoxicity analysis, the ratio of the effector cell and the target cell was 0.625:1 and 5:1, and the ratio of T-cell expressing CAR was 0-70%. The detailed method of the cytotoxicity analysis is the same as the experimental method of Experimental Example 2.

Experimental Result

Figure 6:
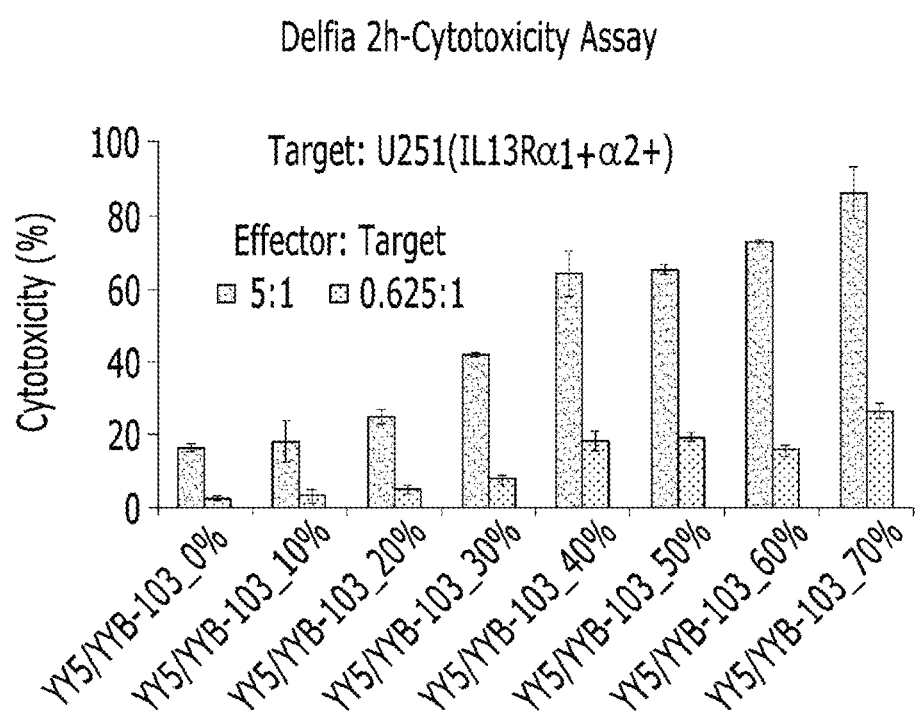
FIG. 6 shows CAR repression rate-dependent anticancer activity increase in human brain cancer cell line U251 of CAR-T cells consisting of IL13 (E11K.R64D.S67D.R107K). TNFRSF9. CD3ζ where four positions are substituted.

In case where T cell expressing IL13Rα2-specific CAR did not exist, 16.4% and 2.5% of cytotoxicity were shown respectively at the ratio of 5:1 and 0.625:1. However, it can be shown that as the ratio of the T cells expressing IL13Rα2-specific CAR increased, the cytotoxicity increased, and it was demonstrated that when the ratio of the T cells expressing IL13Rα2-specific CAR was 70%, 86% and 26% of the cytotoxicity were shown respectively at the ratios of 5:1 and 0.625:1, and thus IL13Rα2-specific chimeric antigen receptor T cell can kill IL13Rα2-specific target cancer cell (U251) (FIG. 6).

Experimental Example 3: Check for the Production of Cytokine (IFN-γ) of T Cells Transformed to IL13Rα2-Specific Chimeric Antigen Receptor Experimental Method 200 ul of a culture medium was put per well in 96 well tissue culture plate, and a target cell (1×10^5) was added. In order to measure cytotoxicity according to CAR expression rate, untransduced activated T cell and 10-70% of CAR-T cell specific to IL13Rα2 were put in the prepared 96 well tissue culture plate with the effector (1×10^5), and cultured at the same time through the duplicate experiment. In addition, in order to verify whether the CAR-T cell shows number-dependent anticancer activity increase, serial dilution was performed from 7500 CAR-T and then put into the effector and cultured at the same time through the duplicate experiment. After 19 hours from the cultivation, the IFN-γ analysis experiment was carried out using the culture supernatant with ELISA analyzer (R&D systems) according to the guidelines of the analyzer manufacturer (FIGS. 7 and 8).

Experimental Result

Generally, the activated T cell generates cytokine that is helpful in its growth and activation, and among them, IFN-γ is secreted by CD8 cell, CD4 T cell and NK cell, etc. and serves an important role in the inherent immune and adaptive immune responses. In particular, this serves an important role in moving T cell to the tumor site as well as inhibiting occurrence of cancer. Through the present experimental example, it was demonstrated whether the generation of IFN-γ is increased when the T cell expressing IL13Rα2-specific CAR met a target cell. According to the experimental method, the T cell expressing IL13Rα2-specific CAR was cultured at the same time as the target cell (HUVEC cell, U251 cell), and then IFN-γ was quantified through the ELISA analysis.

Figure 7:
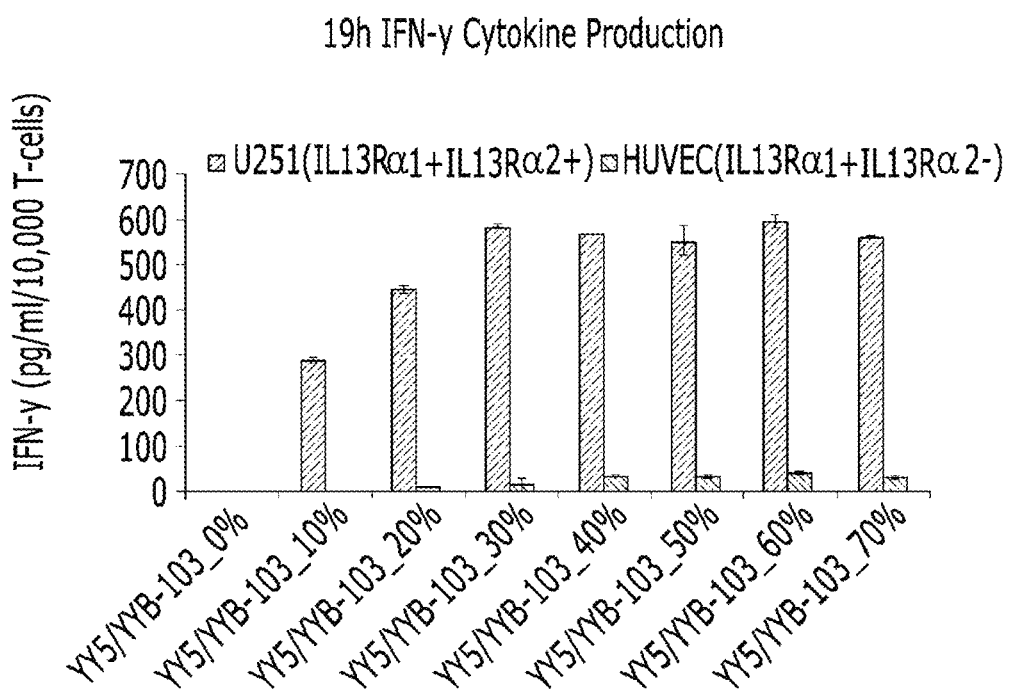
FIG. 7 shows IFN-γ cytokine production after culturing human brain cancer cell line U251 (IL13Rα2 overexpression), which is a target cell with CAR-T cells consisting of IL13(E11K.R64D.S67D.R107K).TNFRSF9.CD3ζ where four positions are substituted or HUVEC (lack of IL13Rα2 expression) which is a normal cell control, at a ratio of 0.5:1 for 19 hours.
Figure 8:
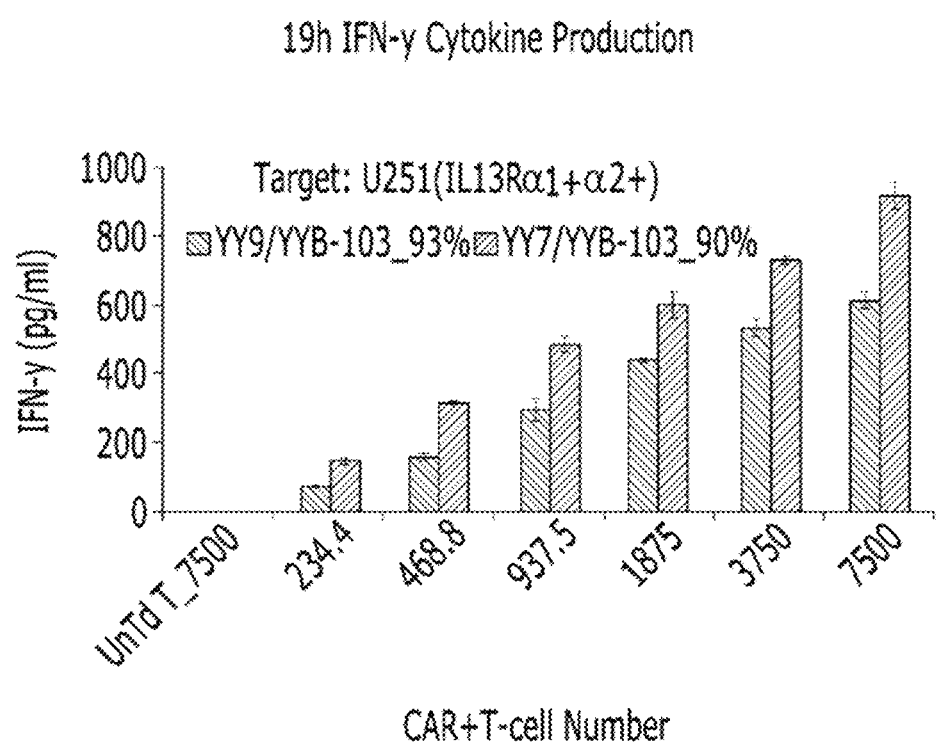
FIG. 8 shows that a dose-dependent (CAR+T-cell number) increase in IFN-γ cytokine secretion, after culturing human brain cancer cell line U251, which is a target cell with CAR-T cells comprising (IL13.E11K.R64D.S67D.R107K).TNFRSF9.CD3ζ where four positions are substituted.

FIG. 7 shows increased IFN-γ when binding to IL13Rα2 antigen according to the transduction ratio of the produced chimeric antigen receptor, and it can be understood that the generation aspects of IFN-γ vary depending on the ratio of the CAR-T cell. In the case of using U251 which is the target cancer cell, the T cell in which the chimeric antigen receptor was untransduced rarely generated IFN-γ. In the case of the T cell in which the chimeric antigen receptor was transduced, the generation of IFN-γ increased by up to 30% ratio, and given that the generation was not increased anymore, it is determined that 30% ratio of the CAR-T cell is sufficient to kill the target cancer cell. Given that in the case of HUVEC which is a cell line that does not overexpress IL13Rα2, even if the ratio of CAR-T increases, the generation of IFN-γ does not increase, it seems that the generation of IFN-γ by CAR-T is specific to IL13Rα2 antigen. FIG. 8 shows increased IFN-γ according to the number of CAR+T cells in two donors, YY6 and YY7, as the number of cells increased, IFN-γ increased. This shows that in killing the cancer cell, the CAR-T cell is dependent on the number of cells.

Example 4: Evaluation of In Vivo Efficacy Using YYB-103

In order to evaluate whether YYB-103 actually exhibits efficacy in vivo, a cancer cell was subcutaneously injected into a nude mouse to induce tumor, and after treating with YYB-103, the change of the tumor size and the persistence of CAR-T cell in the tumor tissue was confirmed.

Experimental Example 1: Production of a Tumor Nude Mouse Using U251 Cell Line and Check for Efficacy of YYB-103

Figure 9A:
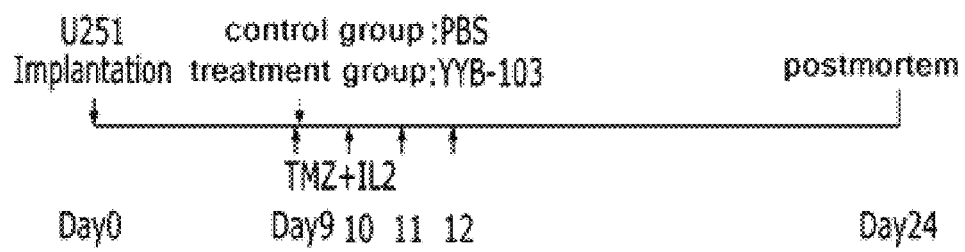
FIG. 9A is an image briefly showing the nude mouse in vivo efficacy experiment method using the CAR-T cells comprising IL13(E11K.R64D.S67D.R107K) TNFRSF9.CD3ζ where four positions are substituted.

The U251 cell line was subcutaneously injected into a nude mouse. After 9 days, control PBS and treatment group YYB-103 were intravenously administered once. Temozolomide (TMZ) and IL-2 were intraperitoneally and intravenously administered into the control group and the experimental group once a day for four days. The size of the tumors was measured after 12 days treatment, and after 15 days treatment, a postmortem was carried out for the measurement of the weight of the tumor tissue and the histologic analysis (FIG. 9)

Experimental Result

Figure 9B:
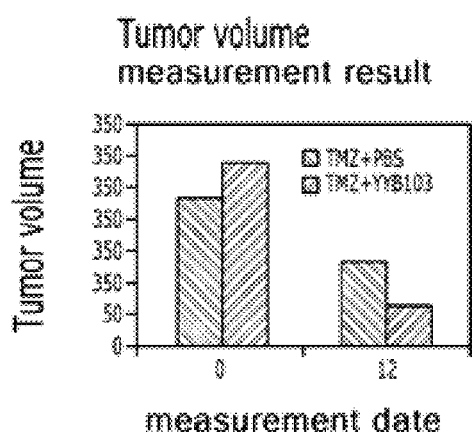
FIG. 9B shows the result of measuring the tumor size of the animal 12 days after the treatment with the CAR-T cell or PBS.
Figure 9C:
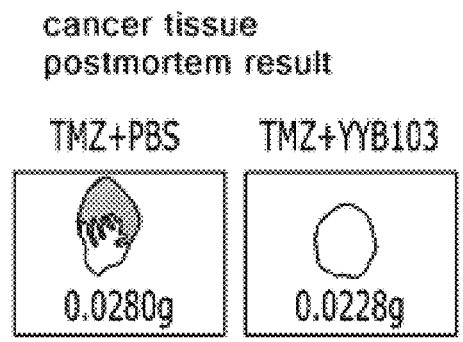
FIG. 9C shows the shape, size and weight of the cancer tissue removed from the nude mouse 15 days after the treatment with the CAR-T cell or PBS.
Figure 11A:
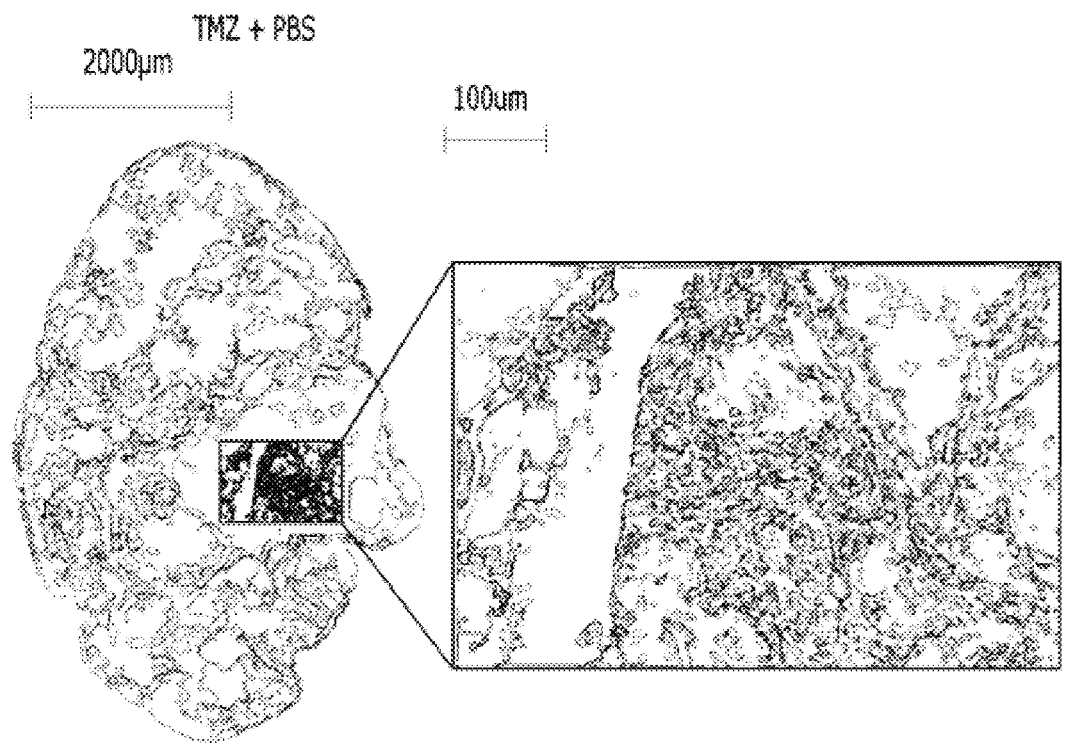
FIG. 11A is an image for the removed cancer tissues stained with H&E from the nude mouse 15 days after the treatment with TMZ+PBS (PBS was intravenously administered once, and TMZ and IL-2 were intraperitoneally and intravenously administered once a day for four days).
Figure 11B:
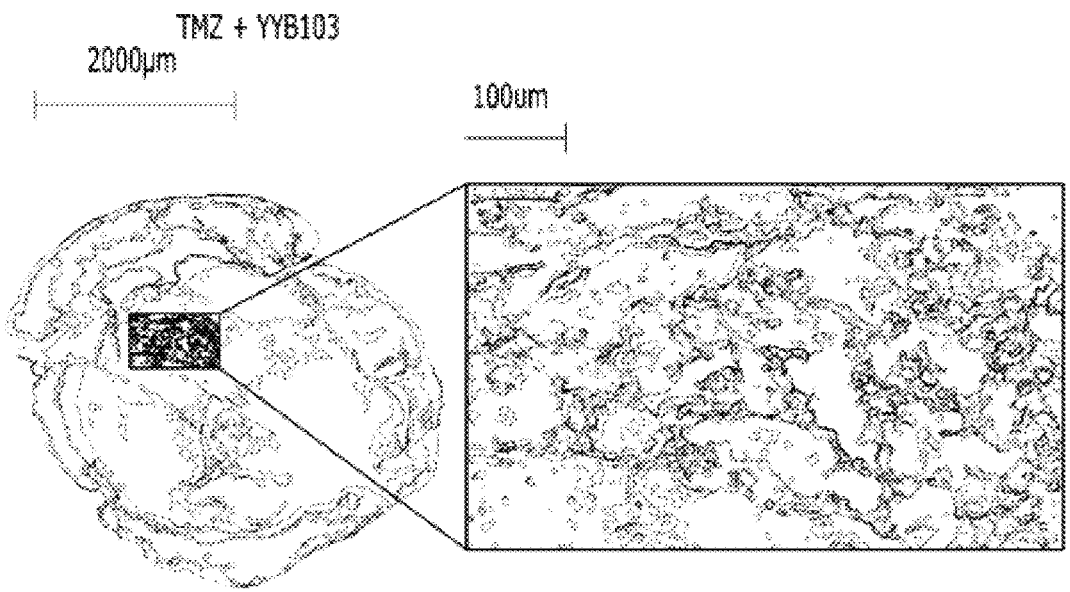
FIG. 11B is an image for the removed cancer tissues stained with H&E from the nude mouse 15 days after the treatment with TMZ+YYB103 (TMZ and CAR-T cell comprising IL13(E11K.R64D.S67D.R107K)TNFRSF9.CD3ζ where four positions are substituted were intravenously administered once, and TMZ and IL-2 were intraperitoneally and intravenously administered once a day for four days).

As the result of measuring the size of the tumor after 12 days treatment to measure efficacy of YYB-103 which was administered into the established subcutaneous tumor nude mouse animal model, in the control group, the size of the tumor was reduced by about 44% from 234.8 mm3 to 132.4 mm3. However, in the case of administering YYB-103 as the treatment group, the size of the tumor was reduced by about 78% from 288.2 mm3 to 64.6 mm3. From this, it can be seen that the treatment group showed the therapeutic effect about 1.8 times as compared to the control group (FIG. 9B). As the result of the measurement of the weight of tumor tissue, obtained by carrying out a postmortem after 15 days treatment, it can be seen that the weight of the tumor tissue of the nude mouse treated with the treatment group, YYB-103, was lighter than the weight of the tumor tissue of the mouse treated with the control group (FIG. 9C). Together with this, when treated with YYB-103, it showed that angiogenesis is inhibited in the tumor tissue, unlike the tumor tissue treated with the control group (FIG. 11A and FIG. 11B).

Figure 10A:
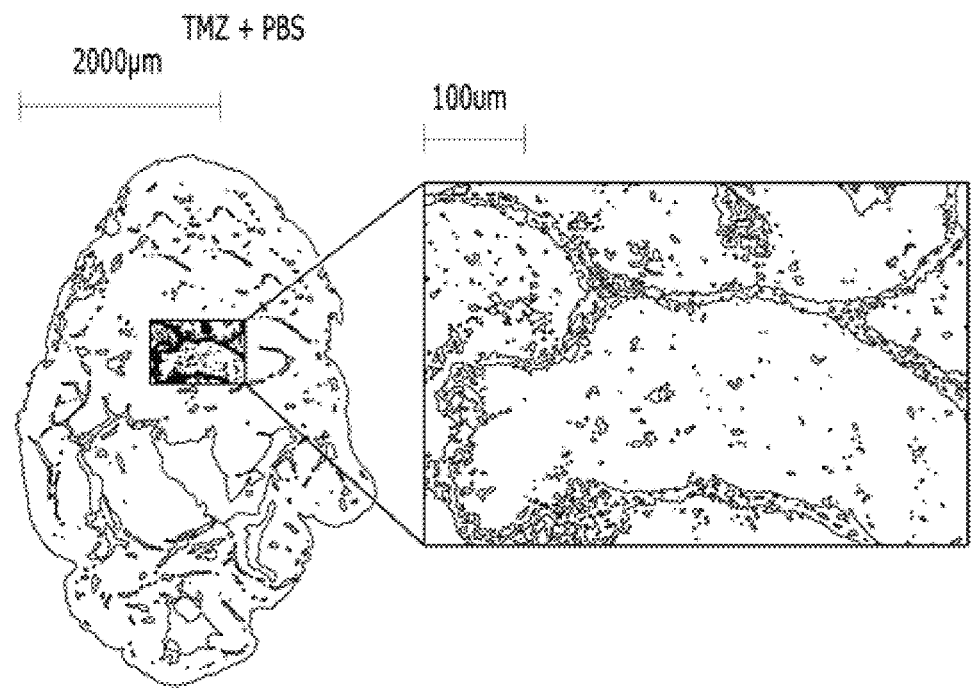
FIG. 10A is an image for the removed cancer tissues stained with anti-human CD3 antibody in order to stain human CAR-T or T cell, from the nude mouse 15 days after the treatment with TMZ+PBS (PBS was intravenously administered once, and TMZ and IL-2 were intraperitoneally and intravenously administered once a day for four days).

In order to verify that YYB-103 persists in the tumor tissue after 15 days treatment, staining was carried out using an anti-human CD3 antibody which is human T cell marker. As the result, it showed that the tumor tissue treated with the control group was not stained because the mouse was free of human T cell (FIG. 10A).

Figure 10B:
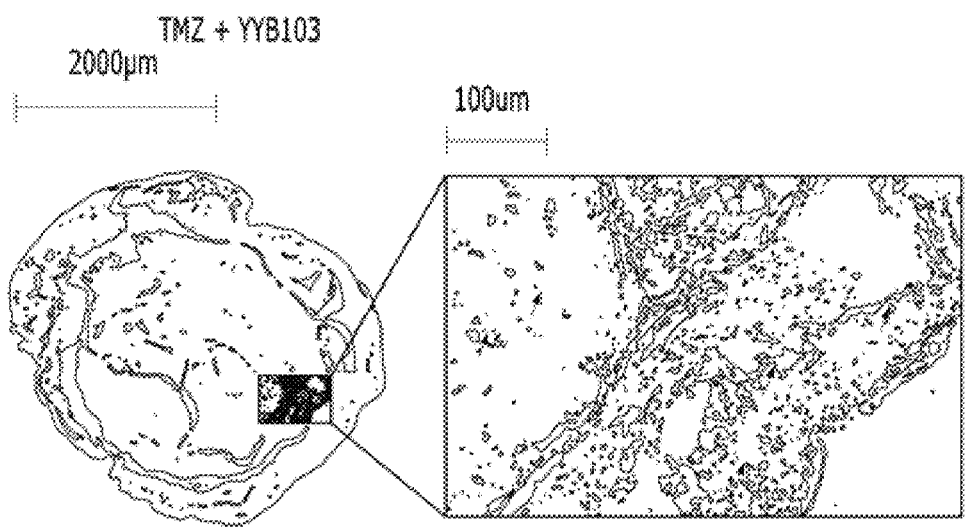
FIG. 10B is an image for the removed cancer tissues stained with anti-human CD3 antibody in order to stain human CAR-T or T cell, from the nude mouse 15 days after the treatment with TMZ+YYB103 (TMZ and CAR-T cell comprising IL13(E11K.R64D.S67D.R107K) TNFRSF9.CD3ζ where four positions are substituted were intravenously administered once, and TMZ and IL-2 were intraperitoneally and intravenously administered once a day for four days).

It was confirmed that the tumor tissue treated with YYB-103, numerous human T cells existed, and this directly gave an influence on the reduction of the size of the tumor treated with YYB-103 (FIG. 10B).

As the result of observing the tumor tissue by H&E staining on the tumor tissue after 15 days treatment, it is seen that in the group that was not treated with YYB-103, many blood vessels were observed. Thus, it seems that due to YYB-103, angiogenesis is inhibited in the tumor site, which results in less aggressive tumor (FIG. 11A & FIG. 11B).

Figure 12A:
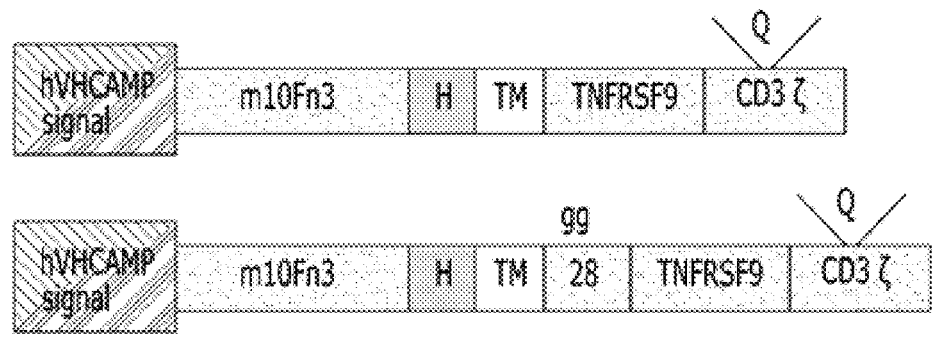
FIG. 12A illustrates the retrovirus vector and transgene representing the main functional element of Anti-Angiogenic CAR.
Figure 12B:
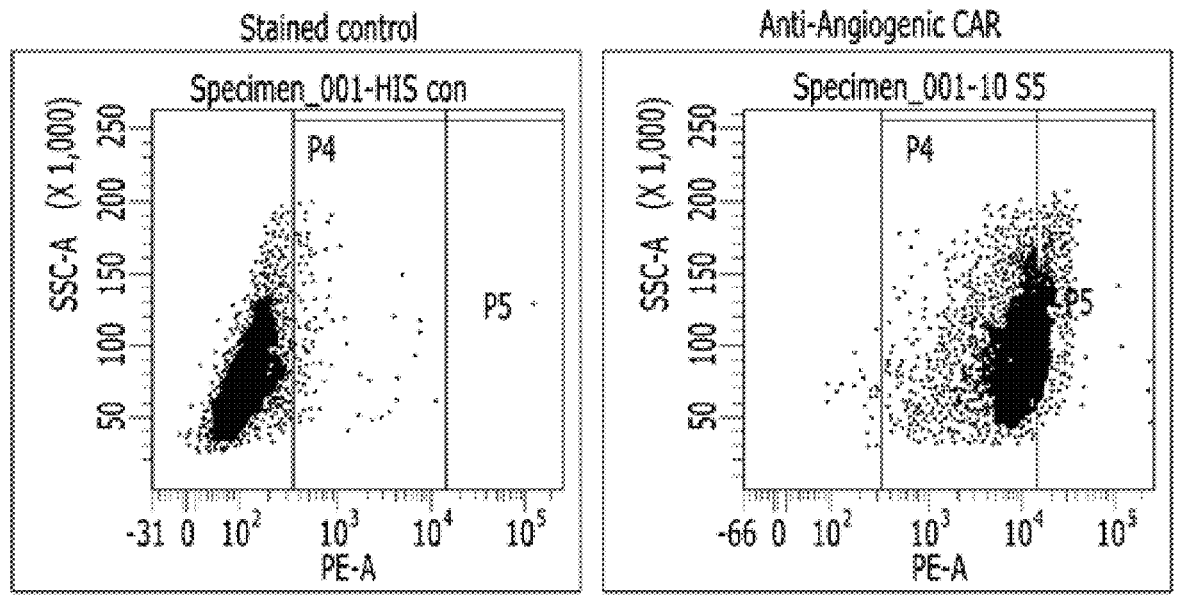
FIG. 12B shows the result of analyzing transformed cells checking on the cell surface expression of Anti-Angiogenic CAR using a Flow cytometry analysis.

Example 5: Construction of CAR Capable of Recognizing Various Solid Tumors and Angiogenic Blood Vessels, and Production of PG13 Cell Line Stably Expressing CAR If angiogenesis which allows new blood vessel to grow in the tumor site is inhibited, the transition and growth of the cancer cell can be inhibited. Successful anti-cancer CAR therapies require not only antigen-specific CAR-T cells but also accessing CAR-T cells to cancer cells and maintaining CAR-T cell function in the immunosuppressive tumor microenvironment. Therefore, anti-angiogenic CAR was produced in order to achieve the object (FIG. 12A).

Figure 13A:
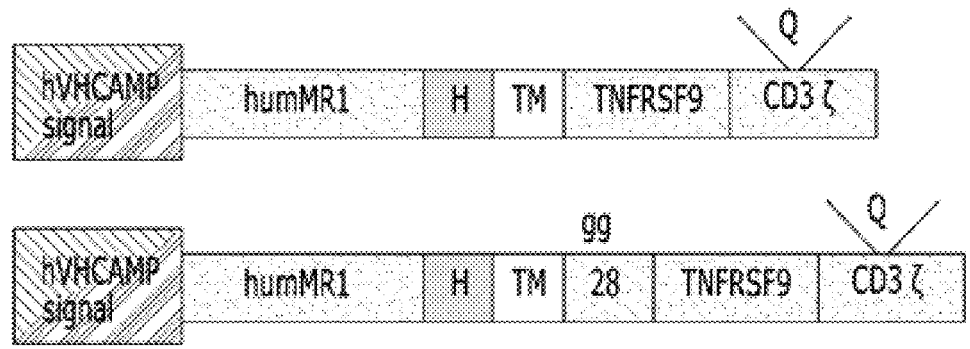
FIGS. 13 to 16 show the four kinds of CAR production, targeting a major tumor antigen of various cancers. A of the respective figures illustrates the retrovirus vector and transgene representing the main functional element; B of the respective figures shows the result of analyzing transformed cells checking on the cell surface expression of Anti-Angiogenic CAR using a Flow cytometry analysis.
Figure 13B:
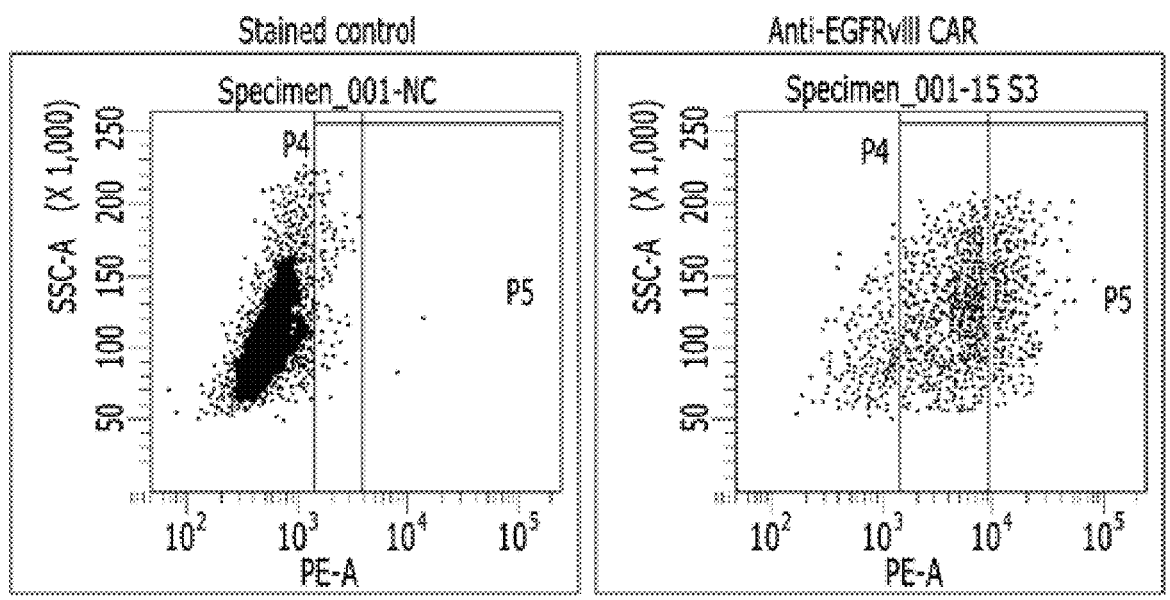

CAR targeting EGFRvIII which is major tumor antigen of glioblastoma, lung cancer, etc. was produced (FIG. 13A).

Figure 14A:
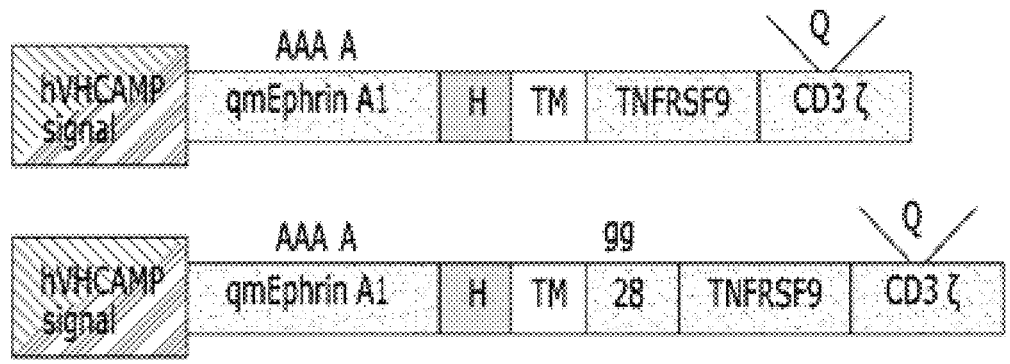
Figure 14B:
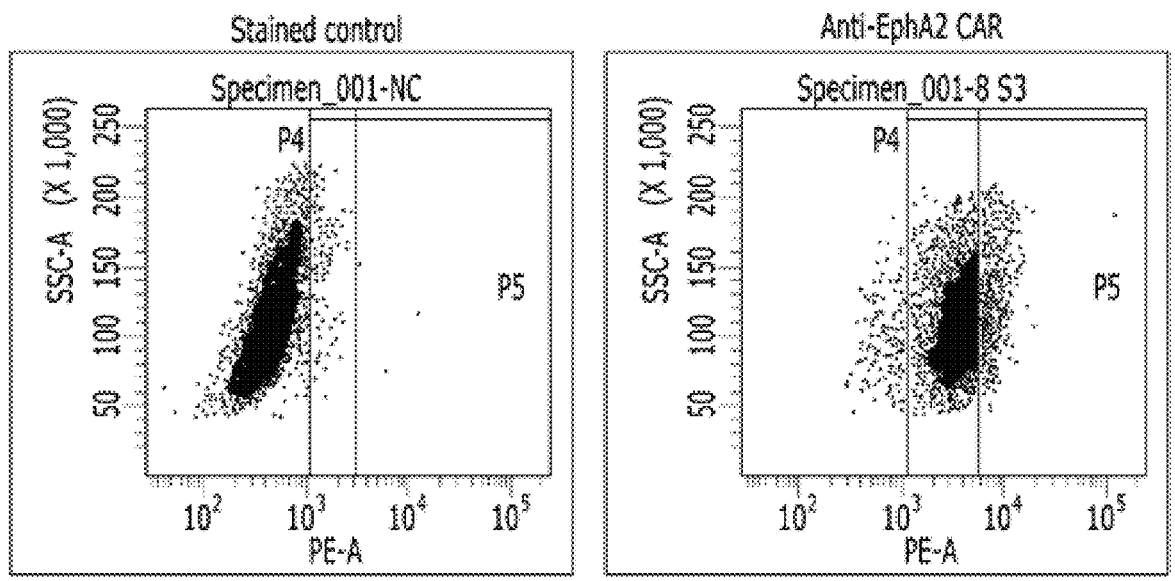

Epha2 (Membrane-bound erythropoietin-producing hepatocellular receptor tyrosine kinase class A2) is overexpressed in breast cancer, prostate cancer, bladder cancer, skin cancer, lung cancer, ovarian cancer, and brain cancer, etc., and thus CAR targeting EphA2 was produced (FIG. 14A).

Figure 15A:
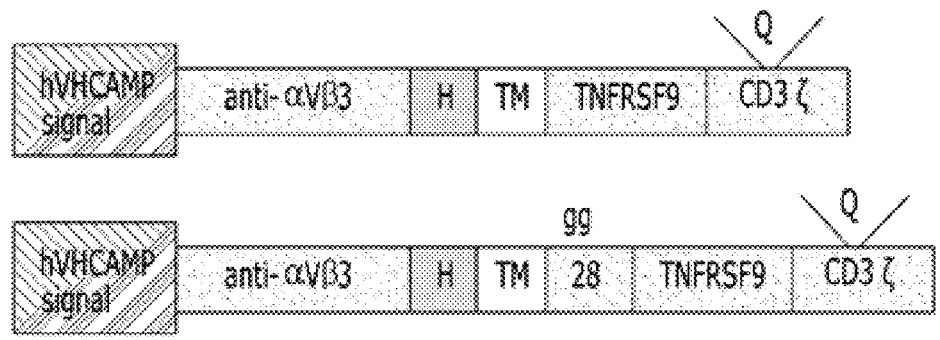
Figure 15B:
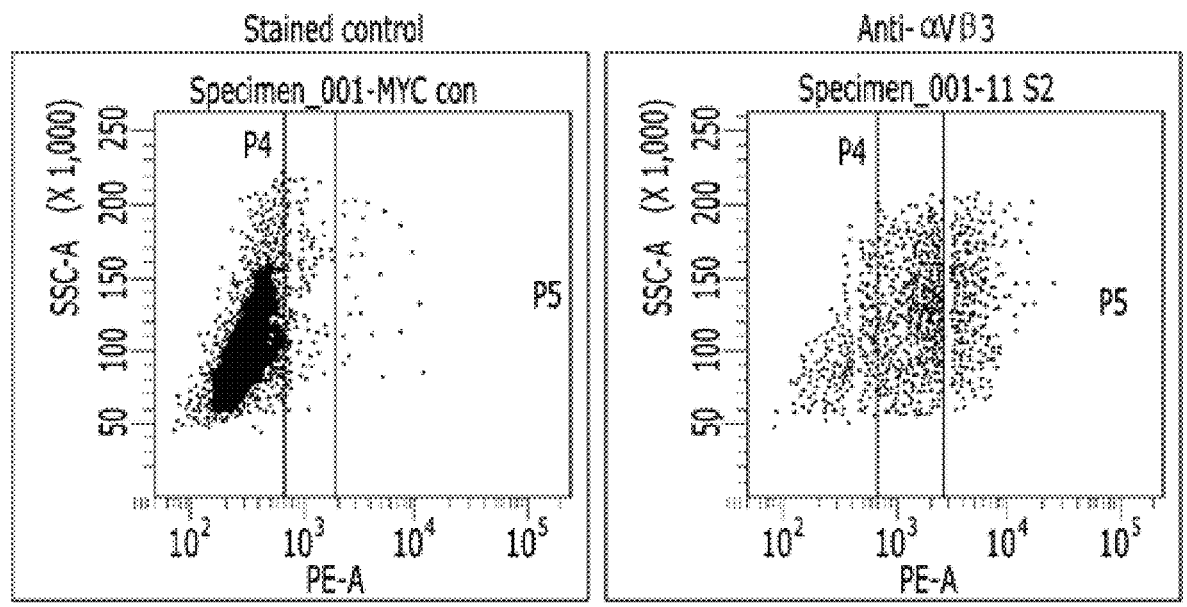

Integrin alpha(V) beta(3) (αVβ3), which is glycoprotein membrane receptor, is highly expressed in activated tumor epithelial cell. CAR targeting αVβ3 which is a resistant marker of carcinoma stemness and receptor tyrosine kinase inhibitors (RTKIs) such as erlotinib of pancreatic cancer, lung cancer and breast cancer was produced (FIG. 15A).

Figure 16A:
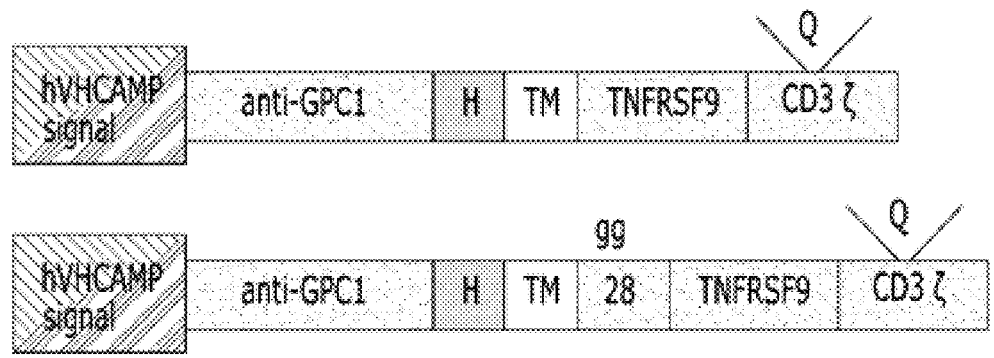
Figure 16B:
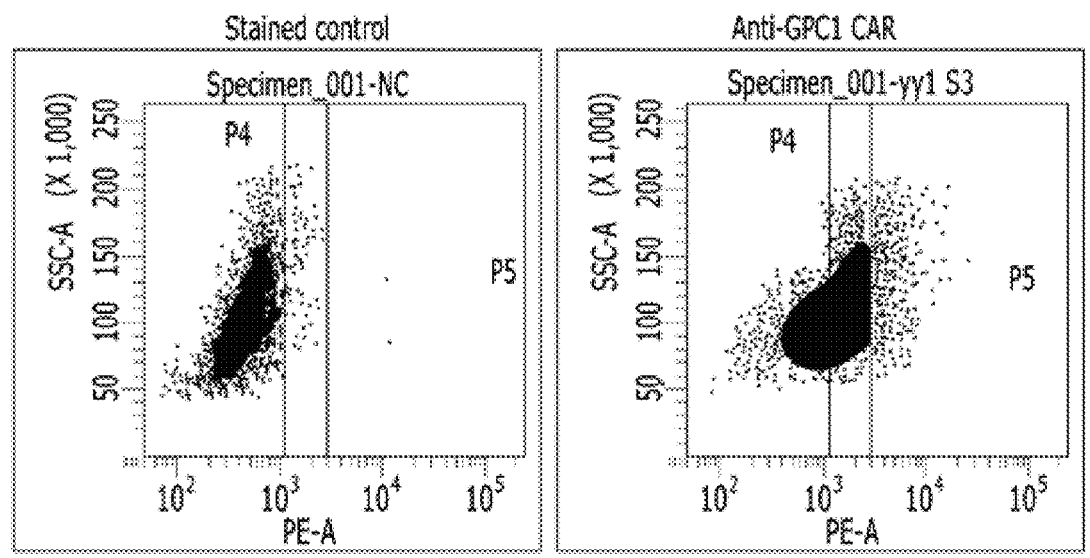

GPC1 is important for efficient growth, transition and angiogenesis of cancer cell, and GPC1 is overexpressed in pancreatic cancer, breast cancer, glioblastoma (FIG. 16A).

Experimental Example 1: Check for CAR Expression Rate on PG13 Cell Surface Transformed to CAR Capable of Recognizing Angiogenic Blood Vessels, EGFRvIII, EphA2, Integrin αVβ3 or GPC1

Experimental Method (Flow Cytometric Analysis)

For flow cytometry (>30,000 events), BD LSRII equipment (Becton Dickinson) and BD FACSDiva software (Becton Dickinson) were used. Specifically, before adding an antibody, the cell was washed once with PBS containing 2% bovine serum albumin. After washing, the cell was reacted with the respective antibodies for 30 minutes at 4° C. in the state where light was blocked and then washed once, and checked the CAR expression rate on PG13 cell surface transformed to CAR, anti-human Fibronectin monoclonal antibody, PE-conjugated anti-human EphA2 monoclonal antibody (R&D Systems) PE-conjugated anti-human alpha v beta 3 monoclonal antibody (BioLegend) was used, and in the case of the antibody where fluorescence is not combined, PE conjugated anti-mouse IgG1 monoclonal antibody (Santa Cruz Biotechnology) or donkey anti-goat IgG phycoerythrin secondary antibody (R&D systems) were additionally used to conduct fluorescence staining.

Experimental Result

As the result of confirming the expression rates of the respective CARs in the transduced PG13 cell line, it was shown that chimeric antigen receptor is expressed on the surface of almost of living PG13 cell lines (FIG. 12B, FIG. 13B, FIG. 14B, FIG. 15B and FIG. 16B).

INDUSTRIAL APPLICABILITY

The present invention relates to CAR-T cells that have been rapidly developed in the cancer treatment field, and is applicable to the medical industry in the patient-specific cancer treatment field.

Sequence Listing Free Text

{Sequence of antigen binding wild type IL-13 domain binding to IL13Rα2}
SEQ ID NO. 1
Length: 112

Type: ligand protein

Name: human

Sequence:
GPVPPSTALRELIEELVNITQNQKAPLCNGSMVWSINLTAGMYCAAL

ESLINVSGCSAIEKTQRMLSGFCPHKVSAGQFSSLHVRDTKIEVAQF

VKDLLLHLKKLFREGQFN

{antigen binding domain capable of binding to an antigen associated with an angiogenic activity}
SEQ ID NO. 2
Length: 92

Type: ligand protein

Name: human

Sequence:
EVVAATPTSLLISWRHPHFPTRYYRITYGETGGNSPVQEFTVLQPPS

TATISGLKPGVDYTITVYAVVERNGRELNTPPISINYRTHHHHHH

{antigen binding domain binding to EGFRvIII}
SEQ ID NO. 3
Length: 252

Type: scFv protein

Name: human

Sequence:
QVQLQESGGGLVKPGGSLKLSCAASGFTFSKFGMSWVRQTPDKRLEW

VASISTGGYNTFYSDNVKGRFTISRDNAKNTLYLQMSSLKSEDTAMY

YCARGYSSTSFAMDYWGQGTMVTVSSGSTSGSGKPGSGEGSDIQMTQ

SPSSLSASVGDRVTITCMTSTDIDDDMNWYQQKPGKTPKLLIYEGNT

LRPGVPSRFSGSGSGTDFIFTISSLQPEDIATYYCLQSFNVPLTFGG

GTKVEIKEQKLISEEDL

{antigen binding domain binding to EphA2}
SEQ ID NO. 4
Length: 141

Type: ligand protein

Name: human

Sequence:
DRHTVFWNSSNPKFRNEDYTIHVQLNDYVDIICPHYEDHSVADAAME

QYILYLVEHEEYQLCQPQSKDQVRWQCNRPSAKHGPEKLSEKFQRFT

AFALAKEFKAGHSYYYISKPIHQHEDRCLRLKVTVSGEQKLISEEDL

{antigen binding domain binding to αVβ3}
SEQ ID NO. 5
Length: 104

Type: ligand protein

Name: human

Sequence:
VSDVPRDLEVVAATPTSLLISWDAPAVTVRYYRITYGETGGNSPVQE

FTVPGSKSTATISGLKPGVDYTITVYAVTPRGDWNEGSKPISINYRT

EQKLISEEDL

{antigen binding domain binding to glypican1}
SEQ ID NO. 6
Length: 418

Type: ligand protein

Name: human

Sequence:
TSPCDNFDCQNGAQCIVRINEPICQCLPGYQGEKCEKLVSVNFINKE

SYLQIPSAKVRPQTNITLQIATDEDSGILLYKGDKDHIAVELYRGRV

RASYDTGSHPASAIYSVETINDGNFHIVELLALDQSLSLSVDGGNPK

IITNLSKQSTLNFDSPLYVGGMPGKSNVASLRQAPGQNGTSFHGCIR

NLYINSELQDFQKVPMQTGILPGCEPCHKKVCAHGTCQPSSQAGFTC

ECQEGWMGPLCDQRTNDPCLGNKCVHGTCLPINAFSYSCKCLEGHGG

VLCDEEEDLFNPCQAIKCKHGKCRLSGLGQPYCECSSGYTGDSCDRE

ISCRGERIRDYYQKQQGYAACQTTKKVSRLECRGGCAGGQCCGPLRS

KRRKYSFECTDGSSFVDEVEKVVKCGCTRCVSEQKLISEEDL

{Wild type CD28}

SEQ ID NO. 7

Length: 41

Type: protein

Name: human

Sequence:
RSKRSRLLHSDYMNMTPRRPGPTRKHYQPYAPPRDFAAYRS

{TNFRSF9}

SEQ ID NO. 8

Length: 42

Type: protein

Name: human

Sequence:
KRGRKKLLYIFKQPFMRPVQTTQEEDGCSCRFPEEEEGGCEL

{hinge region sequence -1}

SEQ ID NO. 9

Length: 47

Type: protein

Name: human

Sequence:
KPTTTPAPRPPTPAPTIASQPLSLRPEACRPAAGGAVHTRGLDFACD

{hinge region sequence-2}

SEQ ID NO. 10

Length: 45

Type: protein

Name: human

Sequence:
KPTTTPAPRPPTPAPTIASQPLSLRPEAARPAAGGAVHTRGLDFA

{transmembrane domain sequence-1}

SEQ ID NO. 11

Length: 21

Type: protein

Name: human

Sequence:
IYIWAPLAGTCGVLLLSLVIT

{transmembrane domain sequence-2}

SEQ ID NO. 12

Length: 23

Type: protein

Name: human

Sequence:
LAYLLDGILFIYGVILTALFLRV

{CD3ζ comprising extra glutamine}

SEQ ID NO. 13

Length: 113

Type: protein

Name: human

Sequence:
RVKFSRSADAPAYQQGQNQLYNELNLGRREEYDVLDKRRGRDPEMGG

KPQRRKNPQEGLYNELQKDKMAEAYSEIGMKGERRRGKGHDGLYQGL

STATKDTYDALHMQALPPR

{YYB 103}

SEQ ID NO. 14

Length: 359

Type: protein

Name: human

Sequence:
MGWSCIILFLVATATGVHSGPVPPSTALRKLIEELVNITQNQKAPLC

NGSMVWSINLTAGMYCAALESLINVSGCSAIEKTQDMLDGFCPHKVS

AGQFSSLHVRDTKIEVAQFVKDLLLHLKKLFKEGQFNGGGPRKPTTT

PAPRPPTPAPTIASQPLSLRPEACRPAAGGAVHTRGLDFACDIYIWA

PLAGTCGVLLLSLVITKRGRKKLLYIFKQPFMRPVQTTQEEDGCSCR

FPEEEEGGCELRVKFSRSADAPAYQQGQNQLYNELNLGRREEYDVLD

KRRGRDPEMGGKPQRRKNPQEGLYNELQKDKMAEAYSEIGMKGERRR

GKGHDGLYQGLSTATKDTYDALHMQALPPR

{YYB 103A}

SEQ ID NO. 15

Length: 400

Type: protein

Name: human

Sequence:
MGWSCIILFLVATATGVHSGPVPPSTALRKLIEELVNITQNQKAPLC

NGSMVWSINLTAGMYCAALESLINVSGCSAIEKTQDMLDGFCPHKVS

AGQFSSLHVRDTKIEVAQFVKDLLLHLKKLFKEGQFNGGGPRKPTTT

PAPRPPTPAPTIASQPLSLRPEACRPAAGGAVHTRGLDFACDIYIWA

PLAGTCGVLLLSLVITRSKRSRGGHSDYMNMTPRRPGPTRKHYQPYA

PPRDFAAYRSKRGRKKLLYIFKQPFMRPVQTTQEEDGCSCRFPEEEE

GGCELRVKFSRSADAPAYQQGQNQLYNELNLGRREEYDVLDKRRGRD

PEMGGKPQRRKNPQEGLYNELQKDKMAEAYSEIGMKGERRRGKGHDG

LYQGLSTATKDTYDALHMQALPPR

{YYB-103B, IL13(E11K.R107K).29.TNFRSF9.CD3ζ}

SEQ ID NO. 16

Length: 400

Type: protein

Name: human

Sequence:
MGWSCIILFLVATATGVHSGPVPPSTALRKLIEELVNITQNQKAPLC

NGSMVWSINLTAGMYCAALESLINVSGCSAIEKTQRMLSGFCPHKVS

AGQFSSLHVRDTKIEVAQFVKDLLLHLKKLFKEGQFNGGGPRKPTTT
PAPRPPTPAPTIASQPLSLRPEACRPAAGGAVHTRGLDFACDIYIWA
PLAGTCGVLLLSLVITRSKRSRGGHSDYMNMTPRRPGPTRKHYQPYA
PPRDFAAYRSKRGRKKLLYIFKQPFMRPVQTTQEEDGCSCRFPEEEE
GGCELRVKFSRSADAPAYQQGQNQLYNELNLGRREEYDVLDKRRGRD
PEMGGKPQRRKNPQEGLYNELQKDKMAEAYSEIGMKGERRRGKGHDG
LYQGLSTATKDTYDALHMQALPPR

{YYB 104}
SEQ ID NO. 17
Length: 339
Type: protein
Name: human
Sequence:
MGWSCIILFLVATATGVHSEVVAATPTSLLISWRHPHFPTRYYRITY
GETGGNSPVQEFTVLQPPSTATISGLKPGVDYTITVYAVVERNGREL
NTPPISINYRTHHHHHGGGPRKPTTTPAPRPPTPAPTIASQPLSLR
PEACRPAAGGAVHTRGLDFACDIYIWAPLAGTCGVLLLSLVITKRGR
KKLLYIFKQPFMRPVQTTQEEDGCSCRFPEEEEGGCELRVKFSRSAD
APAYQQGQNQLYNELNLGRREEYDVLDKRRGRDPEMGGKPQRRKNPQ
EGLYNELQKDKMAEAYSEIGMKGERRRGKGHDGLYQGLSTATKDTYD
ALHMQALPPR {YYB 104-1}
SEQ ID NO. 18
Length: 308
Type: protein
Name: human
Sequence:
MGWSCIILFLVATATGVHSEVVAATPTSLLISWRHPHFPTRYYRITY
GETGGNSPVQEFTVLQPPSTATISGLKPGVDYTITVYAVVERNGREL
NTPPISINYRTHHHHHGGGPRKPTTTPAPRPPTPAPTIASQPLSLR
PEACRPAAGGAVHTRGLDFACDIYIWAPLAGTCGVLLLSLVITRSKR
SRGGHSDYMNMTPRRPGPTRKHYQPYAPPRDFAAYRSKRGRKKLLYI
FKQPFMRPVQTTQEEDGCSCRFPEEEEGGCELRVKFSRSADAPAYQQ
GQNQLYNELNLGRREEYDVLDKRRGRDPEMGGKPQRRKNPQEGLYNE
LQKDKMAEAYSEIGMKGERRRGKGHDGLYQGLSTATKDTYDALHMQA
LPPR {YYB 105}
SEQ ID NO. 19
Length: 497
Type: protein
Name: human Sequence:
MGWSCIILFLVATATGVHSQVQLQESGGGLVKPGGSLKLSCAASGFT
FSKFGMSWVRQTPDKRLEWVASISTGGYNTFYSDNVKGRFTISRDNA
KNTLYLQMSSLKSEDTAMYYCARGYSSTSFAMDYWGQGTMVTVSSGS
TSGSGKPGSGEGSDIQMTQSPSSLSASVGDRVTITCMTSTDIDDDMN
WYQQKPGKTPKLLIYEGNTLRPGVPSRFSGSGSGTDFIFTISSLQPE
DIATYYCLQSFNVPLTFGGGTKVEIKEQKLISEEDLGGGPRKPTTTP
APRPPTPAPTIASQPLSLRPEAARPAAGGAVHTRGLDFALAYLLDGI
LFIYGVILTALFLRVKRGRKKLLYIFKQPFMRPVQTTQEEDGCSCRF
PEEEEGGCELKFSRSADAPAYQQGQNQLYNELNLGRREEYDVLDKRR
GRDPEMGGKPQRRKNPQEGLYNELQKDKMAEAYSEIGMKGERRRGKG
HDGLYQGLSTATKDTYDALHMQALPPR {YYB 105-1}
SEQ ID NO. 20
Length: 538
Type: protein
Name: human
Sequence:
MGWSCIILFLVATATGVHSQVQLQESGGGLVKPGGSLKLSCAASGFT
FSKFGMSWVRQTPDKRLEWVASISTGGYNTFYSDNVKGRFTISRDNA
KNTLYLQMSSLKSEDTAMYYCARGYSSTSFAMDYWGQGTMVTVSSGS
TSGSGKPGSGEGSDIQMTQSPSSLSASVGDRVTITCMTSTDIDDDMN
WYQQKPGKTPKLLIYEGNTLRPGVPSRFSGSGSGTDFIFTISSLQPE
DIATYYCLQSFNVPLTFGGGTKVEIKEQKLISEEDLGGGPRKPTTTP
APRPPTPAPTIASQPLSLRPEAARPAAGGAVHTRGLDFALAYLLDGI
LFIYGVILTALFLRVRSKRSRGGHSDYMNMTPRRPGPTRKHYQPYAP
PRDFAAYRSKRGRKKLLYIFKQPFMRPVQTTQEEDGCSCRFPEEEEG
GCELKFSRSADAPAYQQGQNQLYNELNLGRREEYDVLDKRRGRDPEM
GGKPQRRKNPQEGLYNELQKDKMAEAYSEIGMKGERRRGKGHDGLYQ
GLSTATKDTYDALHMQALPPR {YYB 106}
SEQ ID NO. 21
Length: 388
Type: protein
Name: human
Sequence:
MGWSCIILFLVATATGVHSDRHTVFWNSSNPKFRNEDYTIHVQLNDY
VDIICPHYEDHSVADAAMEQYILYLVEHEEYQLCQPQSKDQVRWQCN
RPSAKHGPEKLSEKFQRFTAFALAKEFKAGHSYYYISKPIHQHEDRC
LRLKVTVSGEQKLISEEDLGGGPRKPTTTPAPRPPTPAPTIASQPLS
LRPEACRPAAGGAVHTRGLDFACDIYIWAPLAGTCGVLLLSLVITKR
GRKKLLYIFKQPFMRPVQTTQEEDGCSCRFPEEEEGGCELRVKFSRS

ADAPAYQQGQNQLYNELNLGRREEYDVLDKRRGRDPEMGGKPQRRKN

PQEGLYNELQKDKMAEAYSEIGMKGERRRGKGHDGLYQGLSTATKDT

YDALHMQALPPR

{YYB 106-1}

SEQ ID NO. 22

Length: 429

Type: protein

Name: human

Sequence:
MGWSCIILFLVATATGVHSDRHTVFWNSSNPKFRNEDYTIHVQLNDY

VDIICPHYEDHSVADAAMEQYILYLVEHEEYQLCQPQSKDQVRWQCN

RPSAKHGPEKLSEKFQRFTAFALAKEFKAGHSYYYISKPIHQHEDRC

LRLKVTVSGEQKLISEEDLGGGPRKPTTTPAPRPPTPAPTIASQPLS

LRPEACRPAAGGAVHTRGLDFACDIYIWAPLAGTCGVLLLSLVITRS

KRSRGGHSDYMNMTPRRPGPTRKHYQPYAPPRDFAAYRSKRGRKKLL

YIFKQPFMRPVQTTQEEDGCSCRFPEEEEGGCELRVKFSRSADAPAY

QQGQNQLYNELNLGRREEYDVLDKRRGRDPEMGGKPQRRKNPQEGLY

NELQKDKMAEAYSEIGMKGERRRGKGHDGLYQGLSTATKDTYDALHM

QALPPR

{YYB 107}

SEQ ID NO. 23

Length: 351

Type: protein

Name: human

Sequence:
MGWSCIILFLVATATGVHSVSDVPRDLEVVAATPTSLLISWDAPAVT

VRYYRITYGETGGNSPVQEFTVPGSKSTATISGLKPGVDYTITVYAV

TPRGDWNEGSKPISINYRTEQKLISEEDLGGGPRKPTTTPAPRPPTP

APTIASQPLSLRPEACRPAAGGAVHTRGLDFACDIYIWAPLAGTCGV

LLLSLVITKRGRKKLLYIFKQPFMRPVQTTQEEDGCSCRFPEEEEGG

CELRVKFSRSADAPAYQQGQNQLYNELNLGRREEYDVLDKRRGRDPE

MGGKPQRRKNPQEGLYNELQKDKMAEAYSEIGMKGERRRGKGHDGLY

QGLSTATKDTYDALHMQALPPR

{YYB 107-1}

SEQ ID NO. 24

Length: 392

Type: protein

Name: human

Sequence:
MGWSCIILFLVATATGVHSVSDVPRDLEVVAATPTSLLISWDAPAVT

VRYYRITYGETGGNSPVQEFTVPGSKSTATISGLKPGVDYTITVYAV

TPRGDWNEGSKPISINYRTEQKLISEEDLGGGPRKPTTTPAPRPPTP

APTIASQPLSLRPEACRPAAGGAVHTRGLDFACDIYIWAPLAGTCGV

LLLSLVITRSKRSRGGHSDYMNMTPRRPGPTRKHYQPYAPPRDFAAY

RSKRGRKKLLYIFKQPFMRPVQTTQEEDGCSCRFPEEEEGGCELRVK

FSRSADAPAYQQGQNQLYNELNLGRREEYDVLDKRRGRDPEMGGKPQ

RRKNPQEGLYNELQKDKMAEAYSEIGMKGERRRGKGHDGLYQGLSTA

TKDTYDALHMQALPPR

{YYB 108}

SEQ ID NO. 25

Length: 665

Type: protein

Name: human

Sequence:
MGWSCIILFLVATATGVHSTSPCDNFDCQNGAQCIVRINEPICQCLP

GYQGEKCEKLVSVNFINKESYLQIPSAKVRPQTNITLQIATDEDSGI

LLYKGDKDHIAVELYRGRVRASYDTGSHPASAIYSVETINDGNFHIV

ELLALDQSLSLSVDGGNPKIITNLSKQSTLNFDSPLYVGGMPGKSNV

ASLRQAPGQNGTSFHGCIRNLYINSELQDFQKVPMQTGILPGCEPCH

KKVCAHGTCQPSSQAGFTCECQEGWMGPLCDQRTNDPCLGNKCVHGT

CLPINAFSYSCKCLEGHGGVLCDEEEDLFNPCQAIKCKHGKCRLSGL

GQPYCECSSGYTGDSCDREISCRGERIRDYYQKQQGYAACQTTKKVS

RLECRGGCAGGQCCGPLRSKRRKYSFECTDGSSFVDEVEKVVKCGCT

RCVSEQKLISEEDLGGGPRKPTTTPAPRPPTPAPTIASQPLSLRPEA

CRPAAGGAVHTRGLDFACDIYIWAPLAGTCGVLLLSLVITKRGRKKL

LYIFKQPFMRPVQTTQEEDGCSCRFPEEEEGGCELRVKFSRSADAPA

YQQGQNQLYNELNLGRREEYDVLDKRRGRDPEMGGKPQRRKNPQEGL

YNELQKDKMAEAYSEIGMKGERRRGKGHDGLYQGLSTATKDTYDALH

MQALPPR

{YYB 108-1}

SEQ ID NO. 26

Length: 706

Type: protein

Name: human

Sequence:
MGWSCIILFLVATATGVHSTSPCDNFDCQNGAQCIVRINEPICQCLP

GYQGEKCEKLVSVNFINKESYLQIPSAKVRPQTNITLQIATDEDSGI

LLYKGDKDHIAVELYRGRVRASYDTGSHPASAIYSVETINDGNFHIV

ELLALDQSLSLSVDGGNPKIITNLSKQSTLNFDSPLYVGGMPGKSNV

ASLRQAPGQNGTSFHGCIRNLYINSELQDFQKVPMQTGILPGCEPCH

KKVCAHGTCQPSSQAGFTCECQEGWMGPLCDQRTNDPCLGNKCVHGT

CLPINAFSYSCKCLEGHGGVLCDEEEDLFNPCQAIKCKHGKCRLSGL

GQPYCECSSGYTGDSCDREISCRGERIRDYYQKQQGYAACQTTKKVS

RLECRGGCAGGQCCGPLRSKRRKYSFECTDGSSFVDEVEKVVKCGCT

| Sequence Listing Free Text |
|---|
| RCVSEQKLISEEDLGGGPRKPTTTPAPRPPTPAPTIASQPLSLRPEA |
| CRPAAGGAVHTRGLDFACDIYIWAPLAGTCGVLLLSLVITRSKRSRG |
| GHSDYMNMTPRRPGPTRKHYQPYAPPRDFAAYRSKRGRKKLLYIFKQ |
| PFMRPVQTTQEEDGCSCRFPEEEEGGCELRVKFSRSADAPAYQQGQN |

| Sequence Listing Free Text |
|---|
| QLYNELNLGRREEYDVLDKRRGRDPEMGGKPQRRKNPQEGLYNELQK |
| DKMAEAYSEIGMKGERRRGKGHDGLYQGLSTATKDTYDALHMQALPP |
| R |

What is claimed is:

1. A chimeric antigen receptor (CAR) comprising an antigen binding domain that binds to IL13Rα2; a hinge region; a transmembrane domain; a costimulatory domain; and a cytoplasmic signaling domain, wherein the antigen binding domain that binds to IL13Rα2 comprises the amino acid sequence set forth in SEQ ID NO: 1 but in which the amino acids at the 11$^{th}$ and 107$^{th}$ positions of SEQ ID NO: 1 are each replaced with lysine and the amino acids at the 64$^{th}$ and 67$^{th}$ positions of SEQ ID NO: 1 are each replaced with aspartic acid.

2. The CAR according to claim 1, wherein the CAR further comprises three glycines between the antigen binding domain and the hinge region.

3. The CAR according to claim 1, wherein the hinge region is a CD8 hinge region comprising the amino acid sequence set forth in SEQ ID NO: 9 or 10.

4. The CAR according to claim 1, wherein the transmembrane domain comprises SEQ ID NO: 11 or SEQ ID NO: 12.

5. The CAR according to claim 1, wherein the costimulatory domain comprises a CD28 costimulatory domain as set forth in SEQ ID NO: 27 and/or a TNFRSF9 costimulatory domain as set forth in SEQ ID NO: 8.

6. The CAR according to claim 1, wherein the cytoplasmic signaling domain is a CD3ζ signaling domain.

7. The CAR according to claim 6, wherein the CD3ζ signaling domain comprises the amino acid sequence set forth in SEQ ID NO: 13.

8. The CAR according to claim 1, wherein the CAR comprises the amino acid sequence set forth in SEQ ID NO: 14.

9. The CAR according to claim 1, wherein the CAR comprises the amino acid sequence set forth in SEQ ID NO: 15.

10. An expression vector encoding the CAR according to claim 1.

11. An expression vector encoding the CAR according to claim 8.

12. An expression vector encoding the CAR according to claim 9.

13. A T cell expressing the CAR according to claim 1.

14. A T cell expressing the CAR according to claim 8.

15. A T cell expressing the CAR according to claim 9.

16. A T cell expressing a chimeric antigen receptor (CAR) comprising the amino acid sequence set forth in SEQ ID NO: 14.

17. A T cell expressing a chimeric antigen receptor (CAR) comprising the amino acid sequence set forth in SEQ ID NO: 15.

18. A method of treating glioblastoma, the method comprising administering to a patient with glioblastoma a therapeutically effective amount of T cells that expresses the CAR according to claim 1.

19. A method of treating glioblastoma, the method comprising administering to a patient with glioblastoma a therapeutically effective amount of T cells that expresses the CAR according to claim 8.

20. A method of treating glioblastoma, the method comprising administering to a patient with glioblastoma a therapeutically effective amount of T cells that expresses the CAR according to claim 9.

* * * * *

SEQUENCE LISTING

<160> NUMBER OF SEQ ID NOS: 27

<210> SEQ ID NO 1
<211> LENGTH: 112
<212> TYPE: PRT
<213> ORGANISM: unknown
<220> FEATURE:
<223> OTHER INFORMATION: HUMAN

<400> SEQUENCE: 1

Gly Pro Val Pro Pro Ser Thr Ala Leu Arg Glu Leu Ile Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Gln Phe Asn
            100                 105                 110

<210> SEQ ID NO 2
<211> LENGTH: 92
<212> TYPE: PRT
<213> ORGANISM: Unknown
<220> FEATURE:
<223> OTHER INFORMATION: HUMAN

<400> SEQUENCE: 2

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Leu Gln Pro Ser Thr
        35                  40                  45

Ala Thr Ile Ser Gly Leu Lys Pro Gly Val Asp Tyr Thr Ile Thr Val
    50                  55                  60

Tyr Ala Val Val Glu Arg Asn Gly Arg Glu Leu Asn Thr Pro Pro Ile
65                  70                  75                  80

Ser Ile Asn Tyr Arg Thr His His His His His His
                85                  90

<210> SEQ ID NO 3
<211> LENGTH: 252
<212> TYPE: PRT

<213> ORGANISM: Unknown
<220> FEATURE:
<223> OTHER INFORMATION: HUMAN

<400> SEQUENCE: 3

```
Gln Val Gln Leu Gln Glu Ser Gly Gly Leu Val Lys Pro Gly Gly
1               5                   10                  15

Ser Leu Lys Leu Ser Cys Ala Ala Ser Gly Phe Thr Phe Ser Lys Phe
            20                  25                  30

Gly Met Ser Trp Val Arg Gln Thr Pro Asp Lys Arg Leu Glu Trp Val
        35                  40                  45

Ala Ser Ile Ser Thr Gly Gly Tyr Asn Thr Phe Tyr Ser Asp Asn Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Gly Tyr Ser Ser Thr Ser Phe Ala Met Asp Tyr Trp Gly Gln
            100                 105                 110

Gly Thr Met Val Thr Val Ser Ser Gly Ser Thr Ser Gly Ser Gly Lys
        115                 120                 125

Pro Gly Ser Gly Glu Gly Ser Asp Ile Gln Met Thr Gln Ser Pro Ser
    130                 135                 140

Ser Leu Ser Ala Ser Val Gly Asp Arg Val Thr Ile Thr Cys Met Thr
145                 150                 155                 160

Ser Thr Asp Ile Asp Asp Asp Met Asn Trp Tyr Gln Gln Lys Pro Gly
                165                 170                 175

Lys Thr Pro Lys Leu Leu Ile Tyr Glu Gly Asn Thr Leu Arg Pro Gly
            180                 185                 190

Val Pro Ser Arg Phe Ser Gly Ser Gly Ser Gly Thr Asp Phe Ile Phe
        195                 200                 205

Thr Ile Ser Ser Leu Gln Pro Glu Asp Ile Ala Thr Tyr Tyr Cys Leu
    210                 215                 220

Gln Ser Phe Asn Val Pro Leu Thr Phe Gly Gly Gly Thr Lys Val Glu
225                 230                 235                 240

Ile Lys Glu Gln Lys Leu Ile Ser Glu Glu Asp Leu
                245                 250
```

<210> SEQ ID NO 4
<211> LENGTH: 141
<212> TYPE: PRT
<213> ORGANISM: Unknown
<220> FEATURE:
<223> OTHER INFORMATION: HUMAN

<400> SEQUENCE: 4

```
Asp Arg His Thr Val Phe Trp Asn Ser Asn Pro Lys Phe Arg Asn
1               5                   10                  15

Glu Asp Tyr Thr Ile His Val Gln Leu Asn Asp Tyr Val Asp Ile Ile
            20                  25                  30

Cys Pro His Tyr Glu Asp His Ser Val Ala Asp Ala Ala Met Glu Gln
        35                  40                  45

Tyr Ile Leu Tyr Leu Val Glu His Glu Glu Tyr Gln Leu Cys Gln Pro
    50                  55                  60

Gln Ser Lys Asp Gln Val Arg Trp Gln Cys Asn Arg Pro Ser Ala Lys
65                  70                  75                  80
```

```
His Gly Pro Glu Lys Leu Ser Glu Lys Phe Gln Arg Phe Thr Ala Phe
                    85                  90                  95

Ala Leu Ala Lys Glu Phe Lys Ala Gly His Ser Tyr Tyr Tyr Ile Ser
            100                 105                 110

Lys Pro Ile His Gln His Glu Asp Arg Cys Leu Arg Leu Lys Val Thr
        115                 120                 125

Val Ser Gly Glu Gln Lys Leu Ile Ser Glu Glu Asp Leu
130                 135                 140

<210> SEQ ID NO 5
<211> LENGTH: 104
<212> TYPE: PRT
<213> ORGANISM: Unknown
<220> FEATURE:
<223> OTHER INFORMATION: HUMAN

<400> SEQUENCE: 5

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
50                  55                  60

Gly Val Asp Tyr Thr Ile Thr Val Tyr Ala Val Thr Pro Arg Gly Asp
65                  70                  75                  80

Trp Asn Glu Gly Ser Lys Pro Ile Ser Ile Asn Tyr Arg Thr Glu Gln
                85                  90                  95

Lys Leu Ile Ser Glu Glu Asp Leu
            100

<210> SEQ ID NO 6
<211> LENGTH: 418
<212> TYPE: PRT
<213> ORGANISM: Unknown
<220> FEATURE:
<223> OTHER INFORMATION: HUMAN

<400> SEQUENCE: 6

Thr Ser Pro Cys Asp Asn Phe Asp Cys Gln Asn Gly Ala Gln Cys Ile
1               5                   10                  15

Val Arg Ile Asn Glu Pro Ile Cys Gln Cys Leu Pro Gly Tyr Gln Gly
            20                  25                  30

Glu Lys Cys Glu Lys Leu Val Ser Val Asn Phe Ile Asn Lys Glu Ser
        35                  40                  45

Tyr Leu Gln Ile Pro Ser Ala Lys Val Arg Pro Gln Thr Asn Ile Thr
    50                  55                  60

Leu Gln Ile Ala Thr Asp Glu Asp Ser Gly Ile Leu Leu Tyr Lys Gly
65                  70                  75                  80

Asp Lys Asp His Ile Ala Val Glu Leu Tyr Arg Gly Arg Val Arg Ala
                85                  90                  95

Ser Tyr Asp Thr Gly Ser His Pro Ala Ser Ala Ile Tyr Ser Val Glu
            100                 105                 110

Thr Ile Asn Asp Gly Asn Phe His Ile Val Glu Leu Leu Ala Leu Asp
        115                 120                 125

Gln Ser Leu Ser Leu Ser Val Asp Gly Gly Asn Pro Lys Ile Ile Thr
    130                 135                 140
```

```
Asn Leu Ser Lys Gln Ser Thr Leu Asn Phe Asp Ser Pro Leu Tyr Val
145                 150                 155                 160

Gly Gly Met Pro Gly Lys Ser Asn Val Ala Ser Leu Arg Gln Ala Pro
            165                 170                 175

Gly Gln Asn Gly Thr Ser Phe His Gly Cys Ile Arg Asn Leu Tyr Ile
        180                 185                 190

Asn Ser Glu Leu Gln Asp Phe Gln Lys Val Pro Met Gln Thr Gly Ile
    195                 200                 205

Leu Pro Gly Cys Glu Pro Cys His Lys Lys Val Cys Ala His Gly Thr
210                 215                 220

Cys Gln Pro Ser Ser Gln Ala Gly Phe Thr Cys Glu Cys Gln Glu Gly
225                 230                 235                 240

Trp Met Gly Pro Leu Cys Asp Gln Arg Thr Asn Asp Pro Cys Leu Gly
            245                 250                 255

Asn Lys Cys Val His Gly Thr Cys Leu Pro Ile Asn Ala Phe Ser Tyr
        260                 265                 270

Ser Cys Lys Cys Leu Glu Gly His Gly Gly Val Leu Cys Asp Glu Glu
    275                 280                 285

Glu Asp Leu Phe Asn Pro Cys Gln Ala Ile Lys Cys Lys His Gly Lys
290                 295                 300

Cys Arg Leu Ser Gly Leu Gly Gln Pro Tyr Cys Glu Cys Ser Ser Gly
305                 310                 315                 320

Tyr Thr Gly Asp Ser Cys Asp Arg Glu Ile Ser Cys Arg Gly Glu Arg
            325                 330                 335

Ile Arg Asp Tyr Tyr Gln Lys Gln Gln Gly Tyr Ala Ala Cys Gln Thr
        340                 345                 350

Thr Lys Lys Val Ser Arg Leu Glu Cys Arg Gly Gly Cys Ala Gly Gly
    355                 360                 365

Gln Cys Cys Gly Pro Leu Arg Ser Lys Arg Arg Lys Tyr Ser Phe Glu
370                 375                 380

Cys Thr Asp Gly Ser Ser Phe Val Asp Glu Val Glu Lys Val Val Lys
385                 390                 395                 400

Cys Gly Cys Thr Arg Cys Val Ser Glu Gln Lys Leu Ile Ser Glu Glu
            405                 410                 415

Asp Leu

<210> SEQ ID NO 7
<211> LENGTH: 41
<212> TYPE: PRT
<213> ORGANISM: Unknown
<220> FEATURE:
<223> OTHER INFORMATION: HUMAN

<400> SEQUENCE: 7

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 8
<211> LENGTH: 42
<212> TYPE: PRT
<213> ORGANISM: Unknown
<220> FEATURE:
```

-continued

<223> OTHER INFORMATION: HUMAN

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 9
<211> LENGTH: 47
<212> TYPE: PRT
<213> ORGANISM: Unknown
<220> FEATURE:
<223> OTHER INFORMATION: HUMAN

<400> SEQUENCE: 9

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp
        35                  40                  45

<210> SEQ ID NO 10
<211> LENGTH: 45
<212> TYPE: PRT
<213> ORGANISM: Unknown
<220> FEATURE:
<223> OTHER INFORMATION: HUMAN

<400> SEQUENCE: 10

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ala Arg Pro Ala
            20                  25                  30

Ala Gly Gly Ala Val His Thr Arg Gly Leu Asp Phe Ala
        35                  40                  45

<210> SEQ ID NO 11
<211> LENGTH: 21
<212> TYPE: PRT
<213> ORGANISM: Unknown
<220> FEATURE:
<223> OTHER INFORMATION: HUMAN

<400> SEQUENCE: 11

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 12
<211> LENGTH: 23
<212> TYPE: PRT
<213> ORGANISM: Unknown
<220> FEATURE:
<223> OTHER INFORMATION: HUMAN

<400> SEQUENCE: 12

Leu Ala Tyr Leu Leu Asp Gly Ile Leu Phe Ile Tyr Gly Val Ile Leu
1               5                   10                  15

```
Thr Ala Leu Phe Leu Arg Val
                20

<210> SEQ ID NO 13
<211> LENGTH: 113
<212> TYPE: PRT
<213> ORGANISM: Unknown
<220> FEATURE:
<223> OTHER INFORMATION: HUMAN

<400> SEQUENCE: 13

Arg Val Lys Phe Ser Arg Ser Ala Asp Ala Pro Ala Tyr Gln Gln Gly
1               5                  10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
        50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 14
<211> LENGTH: 359
<212> TYPE: PRT
<213> ORGANISM: Unknown
<220> FEATURE:
<223> OTHER INFORMATION: HUMAN

<400> SEQUENCE: 14

Met Gly Trp Ser Cys Ile Ile Leu Phe Leu Val Ala Thr Ala Thr Gly
1               5                  10                  15

Val His Ser Gly Pro Val Pro Ser Thr Ala Leu Arg Lys Leu Ile
                20                  25                  30

Glu Glu Leu Val Asn Ile Thr Gln Asn Gln Lys Ala Pro Leu Cys Asn
            35                  40                  45

Gly Ser Met Val Trp Ser Ile Asn Leu Thr Ala Gly Met Tyr Cys Ala
        50                  55                  60

Ala Leu Glu Ser Leu Ile Asn Val Ser Gly Cys Ser Ala Ile Glu Lys
65                  70                  75                  80

Thr Gln Asp Met Leu Asp Gly Phe Cys Pro His Lys Val Ser Ala Gly
                85                  90                  95

Gln Phe Ser Ser Leu His Val Arg Asp Thr Lys Ile Glu Val Ala Gln
            100                 105                 110

Phe Val Lys Asp Leu Leu Leu His Leu Lys Lys Leu Phe Lys Glu Gly
        115                 120                 125

Gln Phe Asn Gly Gly Pro Arg Lys Pro Thr Thr Thr Pro Ala Pro
    130                 135                 140

Arg Pro Pro Thr Pro Ala Pro Thr Ile Ala Ser Gln Pro Leu Ser Leu
145                 150                 155                 160

Arg Pro Glu Ala Cys Arg Pro Ala Ala Gly Gly Ala Val His Thr Arg
                165                 170                 175
```

```
Gly Leu Asp Phe Ala Cys Asp Ile Tyr Ile Trp Ala Pro Leu Ala Gly
            180                 185                 190

Thr Cys Gly Val Leu Leu Ser Leu Val Ile Thr Lys Arg Gly Arg
        195                 200                 205

Lys Lys Leu Leu Tyr Ile Phe Lys Gln Pro Phe Met Arg Pro Val Gln
    210                 215                 220

Thr Thr Gln Glu Glu Asp Gly Cys Ser Cys Arg Phe Pro Glu Glu Glu
225                 230                 235                 240

Glu Gly Gly Cys Glu Leu Arg Val Lys Phe Ser Arg Ser Ala Asp Ala
                245                 250                 255

Pro Ala Tyr Gln Gln Gly Gln Asn Gln Leu Tyr Asn Glu Leu Asn Leu
            260                 265                 270

Gly Arg Arg Glu Glu Tyr Asp Val Leu Asp Lys Arg Gly Arg Asp
        275                 280                 285

Pro Glu Met Gly Gly Lys Pro Gln Arg Arg Lys Asn Pro Gln Glu Gly
            290                 295                 300

Leu Tyr Asn Glu Leu Gln Lys Asp Lys Met Ala Glu Ala Tyr Ser Glu
305                 310                 315                 320

Ile Gly Met Lys Gly Glu Arg Arg Arg Gly Lys Gly His Asp Gly Leu
                325                 330                 335

Tyr Gln Gly Leu Ser Thr Ala Thr Lys Asp Thr Tyr Asp Ala Leu His
            340                 345                 350

Met Gln Ala Leu Pro Pro Arg
        355

<210> SEQ ID NO 15
<211> LENGTH: 400
<212> TYPE: PRT
<213> ORGANISM: Unknown
<220> FEATURE:
<223> OTHER INFORMATION: HUMAN

<400> SEQUENCE: 15

Met Gly Trp Ser Cys Ile Ile Leu Phe Leu Val Ala Thr Ala Thr Gly
1               5                   10                  15

Val His Ser Gly Pro Val Pro Ser Thr Ala Leu Arg Lys Leu Ile
            20                  25                  30

Glu Glu Leu Val Asn Ile Thr Gln Asn Gln Lys Ala Pro Leu Cys Asn
        35                  40                  45

Gly Ser Met Val Trp Ser Ile Asn Leu Thr Ala Gly Met Tyr Cys Ala
    50                  55                  60

Ala Leu Glu Ser Leu Ile Asn Val Ser Gly Cys Ser Ala Ile Glu Lys
65                  70                  75                  80

Thr Gln Asp Met Leu Asp Gly Phe Cys Pro His Lys Val Ser Ala Gly
                85                  90                  95

Gln Phe Ser Ser Leu His Val Arg Asp Thr Lys Ile Glu Val Ala Gln
            100                 105                 110

Phe Val Lys Asp Leu Leu Leu His Leu Lys Lys Leu Phe Lys Glu Gly
        115                 120                 125

Gln Phe Asn Gly Gly Gly Pro Arg Lys Pro Thr Thr Thr Pro Ala Pro
    130                 135                 140

Arg Pro Pro Thr Pro Ala Pro Thr Ile Ala Ser Gln Pro Leu Ser Leu
145                 150                 155                 160

Arg Pro Glu Ala Cys Arg Pro Ala Ala Gly Gly Ala Val His Thr Arg
                165                 170                 175
```

Gly Leu Asp Phe Ala Cys Asp Ile Tyr Ile Trp Ala Pro Leu Ala Gly
                180                 185                 190

Thr Cys Gly Val Leu Leu Ser Leu Val Ile Thr Arg Ser Lys Arg
        195                 200                 205

Ser Arg Gly Gly His Ser Asp Tyr Met Asn Met Thr Pro Arg Pro
210                 215                 220

Gly Pro Thr Arg Lys His Tyr Gln Pro Tyr Ala Pro Pro Arg Asp Phe
225                 230                 235                 240

Ala Ala Tyr Arg Ser Lys Arg Gly Arg Lys Lys Leu Leu Tyr Ile Phe
                245                 250                 255

Lys Gln Pro Phe Met Arg Pro Val Gln Thr Thr Gln Glu Glu Asp Gly
                260                 265                 270

Cys Ser Cys Arg Phe Pro Glu Glu Glu Gly Gly Cys Glu Leu Arg
        275                 280                 285

Val Lys Phe Ser Arg Ser Ala Asp Ala Pro Ala Tyr Gln Gln Gly Gln
        290                 295                 300

Asn Gln Leu Tyr Asn Glu Leu Asn Leu Gly Arg Arg Glu Glu Tyr Asp
305                 310                 315                 320

Val Leu Asp Lys Arg Arg Gly Arg Asp Pro Glu Met Gly Gly Lys Pro
                325                 330                 335

Gln Arg Arg Lys Asn Pro Gln Glu Gly Leu Tyr Asn Glu Leu Gln Lys
                340                 345                 350

Asp Lys Met Ala Glu Ala Tyr Ser Glu Ile Gly Met Lys Gly Glu Arg
                355                 360                 365

Arg Arg Gly Lys Gly His Asp Gly Leu Tyr Gln Gly Leu Ser Thr Ala
            370                 375                 380

Thr Lys Asp Thr Tyr Asp Ala Leu His Met Gln Ala Leu Pro Pro Arg
385                 390                 395                 400

<210> SEQ ID NO 16
<211> LENGTH: 400
<212> TYPE: PRT
<213> ORGANISM: Unknown
<220> FEATURE:
<223> OTHER INFORMATION: HUMAN

<400> SEQUENCE: 16

Met Gly Trp Ser Cys Ile Ile Leu Phe Leu Val Ala Thr Ala Thr Gly
1               5                   10                  15

Val His Ser Gly Pro Val Pro Ser Thr Ala Leu Arg Lys Leu Ile
            20                  25                  30

Glu Glu Leu Val Asn Ile Thr Gln Asn Gln Lys Ala Pro Leu Cys Asn
                35                  40                  45

Gly Ser Met Val Trp Ser Ile Asn Leu Thr Ala Gly Met Tyr Cys Ala
        50                  55                  60

Ala Leu Glu Ser Leu Ile Asn Val Ser Gly Cys Ser Ala Ile Glu Lys
65                  70                  75                  80

Thr Gln Arg Met Leu Ser Gly Phe Cys Pro His Lys Val Ser Ala Gly
                85                  90                  95

Gln Phe Ser Ser Leu His Val Arg Asp Thr Lys Ile Glu Val Ala Gln
            100                 105                 110

Phe Val Lys Asp Leu Leu Leu His Leu Lys Lys Leu Phe Lys Glu Gly
            115                 120                 125

Gln Phe Asn Gly Gly Gly Pro Arg Lys Pro Thr Thr Thr Pro Ala Pro
        130                 135                 140

```
Arg Pro Pro Thr Pro Ala Pro Thr Ile Ala Ser Gln Pro Leu Ser Leu
145                 150                 155                 160

Arg Pro Glu Ala Cys Arg Pro Ala Ala Gly Ala Val His Thr Arg
            165                 170                 175

Gly Leu Asp Phe Ala Cys Asp Ile Tyr Ile Trp Ala Pro Leu Ala Gly
            180                 185                 190

Thr Cys Gly Val Leu Leu Leu Ser Leu Val Ile Thr Arg Ser Lys Arg
        195                 200                 205

Ser Arg Gly Gly His Ser Asp Tyr Met Asn Met Thr Pro Arg Arg Pro
210                 215                 220

Gly Pro Thr Arg Lys His Tyr Gln Pro Tyr Ala Pro Pro Arg Asp Phe
225                 230                 235                 240

Ala Ala Tyr Arg Ser Lys Arg Gly Arg Lys Lys Leu Leu Tyr Ile Phe
                245                 250                 255

Lys Gln Pro Phe Met Arg Pro Val Gln Thr Thr Gln Glu Glu Asp Gly
                260                 265                 270

Cys Ser Cys Arg Phe Pro Glu Glu Glu Glu Gly Gly Cys Glu Leu Arg
        275                 280                 285

Val Lys Phe Ser Arg Ser Ala Asp Ala Pro Ala Tyr Gln Gln Gly Gln
290                 295                 300

Asn Gln Leu Tyr Asn Glu Leu Asn Leu Gly Arg Arg Glu Glu Tyr Asp
305                 310                 315                 320

Val Leu Asp Lys Arg Arg Gly Arg Asp Pro Glu Met Gly Gly Lys Pro
                325                 330                 335

Gln Arg Arg Lys Asn Pro Gln Glu Gly Leu Tyr Asn Glu Leu Gln Lys
                340                 345                 350

Asp Lys Met Ala Glu Ala Tyr Ser Glu Ile Gly Met Lys Gly Glu Arg
            355                 360                 365

Arg Arg Gly Lys Gly His Asp Gly Leu Tyr Gln Gly Leu Ser Thr Ala
        370                 375                 380

Thr Lys Asp Thr Tyr Asp Ala Leu His Met Gln Ala Leu Pro Pro Arg
385                 390                 395                 400

<210> SEQ ID NO 17
<211> LENGTH: 339
<212> TYPE: PRT
<213> ORGANISM: Unknown
<220> FEATURE:
<223> OTHER INFORMATION: HUMAN

<400> SEQUENCE: 17

Met Gly Trp Ser Cys Ile Ile Leu Phe Leu Val Ala Thr Ala Thr Gly
1               5                   10                  15

Val His Ser Glu Val Val Ala Ala Thr Pro Thr Ser Leu Leu Ile Ser
            20                  25                  30

Trp Arg His Pro His Phe Pro Thr Arg Tyr Tyr Arg Ile Thr Tyr Gly
        35                  40                  45

Glu Thr Gly Gly Asn Ser Pro Val Gln Glu Phe Thr Val Leu Gln Pro
50                  55                  60

Pro Ser Thr Ala Thr Ile Ser Gly Leu Lys Pro Gly Val Asp Tyr Thr
65                  70                  75                  80

Ile Thr Val Tyr Ala Val Val Glu Arg Asn Gly Arg Glu Leu Asn Thr
                85                  90                  95

Pro Pro Ile Ser Ile Asn Tyr Arg Thr His His His His His His Gly
                100                 105                 110
```

```
Gly Gly Pro Arg Lys Pro Thr Thr Thr Pro Ala Pro Arg Pro Pro Thr
            115                 120                 125

Pro Ala Pro Thr Ile Ala Ser Gln Pro Leu Ser Leu Arg Pro Glu Ala
        130                 135                 140

Cys Arg Pro Ala Ala Gly Gly Ala Val His Thr Arg Gly Leu Asp Phe
145                 150                 155                 160

Ala Cys Asp Ile Tyr Ile Trp Ala Pro Leu Ala Gly Thr Cys Gly Val
                165                 170                 175

Leu Leu Leu Ser Leu Val Ile Thr Lys Arg Gly Arg Lys Lys Leu Leu
                180                 185                 190

Tyr Ile Phe Lys Gln Pro Phe Met Arg Pro Val Gln Thr Thr Gln Glu
                195                 200                 205

Glu Asp Gly Cys Ser Cys Arg Phe Pro Glu Glu Glu Glu Gly Gly Cys
            210                 215                 220

Glu Leu Arg Val Lys Phe Ser Arg Ser Ala Asp Ala Pro Ala Tyr Gln
225                 230                 235                 240

Gln Gly Gln Asn Gln Leu Tyr Asn Glu Leu Asn Leu Gly Arg Arg Glu
                245                 250                 255

Glu Tyr Asp Val Leu Asp Lys Arg Arg Gly Arg Asp Pro Glu Met Gly
                260                 265                 270

Gly Lys Pro Gln Arg Arg Lys Asn Pro Gln Glu Gly Leu Tyr Asn Glu
            275                 280                 285

Leu Gln Lys Asp Lys Met Ala Glu Ala Tyr Ser Glu Ile Gly Met Lys
            290                 295                 300

Gly Glu Arg Arg Arg Gly Lys Gly His Asp Gly Leu Tyr Gln Gly Leu
305                 310                 315                 320

Ser Thr Ala Thr Lys Asp Thr Tyr Asp Ala Leu His Met Gln Ala Leu
                325                 330                 335

Pro Pro Arg

<210> SEQ ID NO 18
<211> LENGTH: 380
<212> TYPE: PRT
<213> ORGANISM: Unknown
<220> FEATURE:
<223> OTHER INFORMATION: HUMAN

<400> SEQUENCE: 18

Met Gly Trp Ser Cys Ile Ile Leu Phe Leu Val Ala Thr Ala Thr Gly
1               5                   10                  15

Val His Ser Glu Val Val Ala Ala Pro Thr Ser Leu Leu Ile Ser
                20                  25                  30

Trp Arg His Pro His Phe Pro Thr Arg Tyr Tyr Arg Ile Thr Tyr Gly
                35                  40                  45

Glu Thr Gly Gly Asn Ser Pro Val Gln Glu Phe Thr Val Leu Gln Pro
        50                  55                  60

Pro Ser Thr Ala Thr Ile Ser Gly Leu Lys Pro Gly Val Asp Tyr Thr
65                  70                  75                  80

Ile Thr Val Tyr Ala Val Val Glu Arg Asn Gly Arg Glu Leu Asn Thr
                85                  90                  95

Pro Pro Ile Ser Ile Asn Tyr Arg Thr His His His His His His Gly
            100                 105                 110

Gly Gly Pro Arg Lys Pro Thr Thr Thr Pro Ala Pro Arg Pro Pro Thr
            115                 120                 125
```

```
Pro Ala Pro Thr Ile Ala Ser Gln Pro Leu Ser Leu Arg Pro Glu Ala
        130                 135                 140

Cys Arg Pro Ala Ala Gly Gly Ala Val His Thr Arg Gly Leu Asp Phe
145                 150                 155                 160

Ala Cys Asp Ile Tyr Ile Trp Ala Pro Leu Ala Gly Thr Cys Gly Val
                165                 170                 175

Leu Leu Leu Ser Leu Val Ile Thr Arg Ser Lys Arg Ser Arg Gly Gly
            180                 185                 190

His Ser Asp Tyr Met Asn Met Thr Pro Arg Arg Pro Gly Pro Thr Arg
        195                 200                 205

Lys His Tyr Gln Pro Tyr Ala Pro Pro Arg Asp Phe Ala Ala Tyr Arg
    210                 215                 220

Ser Lys Arg Gly Arg Lys Lys Leu Leu Tyr Ile Phe Lys Gln Pro Phe
225                 230                 235                 240

Met Arg Pro Val Gln Thr Thr Gln Glu Glu Asp Gly Cys Ser Cys Arg
                245                 250                 255

Phe Pro Glu Glu Glu Glu Gly Gly Cys Glu Leu Arg Val Lys Phe Ser
            260                 265                 270

Arg Ser Ala Asp Ala Pro Ala Tyr Gln Gln Gly Gln Asn Gln Leu Tyr
    275                 280                 285

Asn Glu Leu Asn Leu Gly Arg Arg Glu Glu Tyr Asp Val Leu Asp Lys
290                 295                 300

Arg Arg Gly Arg Asp Pro Glu Met Gly Gly Lys Pro Gln Arg Arg Lys
305                 310                 315                 320

Asn Pro Gln Glu Gly Leu Tyr Asn Glu Leu Gln Lys Asp Lys Met Ala
                325                 330                 335

Glu Ala Tyr Ser Glu Ile Gly Met Lys Gly Glu Arg Arg Arg Gly Lys
            340                 345                 350

Gly His Asp Gly Leu Tyr Gln Gly Leu Ser Thr Ala Thr Lys Asp Thr
    355                 360                 365

Tyr Asp Ala Leu His Met Gln Ala Leu Pro Pro Arg
            370                 375             380

<210> SEQ ID NO 19
<211> LENGTH: 497
<212> TYPE: PRT
<213> ORGANISM: Unknown
<220> FEATURE:
<223> OTHER INFORMATION: HUMAN

<400> SEQUENCE: 19

Met Gly Trp Ser Cys Ile Ile Leu Phe Leu Val Ala Thr Ala Thr Gly
1               5                   10                  15

Val His Ser Gln Val Gln Leu Gln Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Lys Phe Gly Met Ser Trp Val Arg Gln Thr Pro Asp Lys Arg Leu
    50                  55                  60

Glu Trp Val Ala Ser Ile Ser Thr Gly Gly Tyr Asn Thr Phe Tyr Ser
65                  70                  75                  80

Asp Asn Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110
```

```
Tyr Tyr Cys Ala Arg Gly Tyr Ser Thr Ser Phe Ala Met Asp Tyr
            115                 120                 125

Trp Gly Gln Gly Thr Met Val Thr Val Ser Ser Gly Ser Thr Ser Gly
130                 135                 140

Ser Gly Lys Pro Gly Ser Gly Glu Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Met Thr Ser Thr Asp Ile Asp Asp Met Asn Trp Tyr Gln Gln
            180                 185                 190

Lys Pro Gly Lys Thr Pro Lys Leu Leu Ile Tyr Glu Gly Asn Thr Leu
                195                 200                 205

Arg Pro Gly Val Pro Ser Arg Phe Ser Gly Ser Gly Ser Gly Thr Asp
210                 215                 220

Phe Ile Phe Thr Ile Ser Ser Leu Gln Pro Glu Asp Ile Ala Thr Tyr
225                 230                 235                 240

Tyr Cys Leu Gln Ser Phe Asn Val Pro Leu Thr Phe Gly Gly Gly Thr
            245                 250                 255

Lys Val Glu Ile Lys Glu Gln Lys Leu Ile Ser Glu Glu Asp Leu Gly
            260                 265                 270

Gly Gly Pro Arg Lys Pro Thr Thr Thr Pro Ala Pro Arg Pro Pro Thr
            275                 280                 285

Pro Ala Pro Thr Ile Ala Ser Gln Pro Leu Ser Leu Arg Pro Glu Ala
290                 295                 300

Ala Arg Pro Ala Ala Gly Gly Ala Val His Thr Arg Gly Leu Asp Phe
305                 310                 315                 320

Ala Leu Ala Tyr Leu Leu Asp Gly Ile Leu Phe Ile Tyr Gly Val Ile
                325                 330                 335

Leu Thr Ala Leu Phe Leu Arg Val Lys Arg Gly Arg Lys Lys Leu Leu
            340                 345                 350

Tyr Ile Phe Lys Gln Pro Phe Met Arg Pro Val Gln Thr Thr Gln Glu
            355                 360                 365

Glu Asp Gly Cys Ser Cys Arg Phe Pro Glu Glu Glu Glu Gly Gly Cys
370                 375                 380

Glu Leu Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
                420                 425                 430

Pro Gln Arg Arg Lys Asn Pro Gln Glu Gly Leu Tyr Asn Glu Leu Gln
                435                 440                 445

Lys Asp Lys Met Ala Glu Ala Tyr Ser Glu Ile Gly Met Lys Gly Glu
450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 20
<211> LENGTH: 538
<212> TYPE: PRT
<213> ORGANISM: Unknown
```

-continued

<220> FEATURE:
<223> OTHER INFORMATION: HUMAN

<400> SEQUENCE: 20

```
Met Gly Trp Ser Cys Ile Ile Leu Phe Leu Val Ala Thr Ala Thr Gly
1               5                   10                  15

Val His Ser Gln Val Gln Leu Gln Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Lys Phe Gly Met Ser Trp Val Arg Gln Thr Pro Asp Lys Arg Leu
    50                  55                  60

Glu Trp Val Ala Ser Ile Ser Thr Gly Gly Tyr Asn Thr Phe Tyr Ser
65                  70                  75                  80

Asp Asn Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Gly Tyr Ser Ser Thr Ser Phe Ala Met Asp Tyr
        115                 120                 125

Trp Gly Gln Gly Thr Met Val Thr Val Ser Ser Gly Ser Thr Ser Gly
    130                 135                 140

Ser Gly Lys Pro Gly Ser Gly Glu Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Met Thr Ser Thr Asp Ile Asp Asp Asp Met Asn Trp Tyr Gln Gln
            180                 185                 190

Lys Pro Gly Lys Thr Pro Lys Leu Leu Ile Tyr Glu Gly Asn Thr Leu
        195                 200                 205

Arg Pro Gly Val Pro Ser Arg Phe Ser Gly Ser Gly Ser Gly Thr Asp
    210                 215                 220

Phe Ile Phe Thr Ile Ser Ser Leu Gln Pro Glu Asp Ile Ala Thr Tyr
225                 230                 235                 240

Tyr Cys Leu Gln Ser Phe Asn Val Pro Leu Thr Phe Gly Gly Gly Thr
                245                 250                 255

Lys Val Glu Ile Lys Glu Gln Lys Leu Ile Ser Glu Glu Asp Leu Gly
            260                 265                 270

Gly Gly Pro Arg Lys Pro Thr Thr Thr Pro Ala Pro Arg Pro Pro Thr
        275                 280                 285

Pro Ala Pro Thr Ile Ala Ser Gln Pro Leu Ser Leu Arg Pro Glu Ala
    290                 295                 300

Ala Arg Pro Ala Ala Gly Gly Ala Val His Thr Arg Gly Leu Asp Phe
305                 310                 315                 320

Ala Leu Ala Tyr Leu Leu Asp Gly Ile Leu Phe Ile Tyr Gly Val Ile
                325                 330                 335

Leu Thr Ala Leu Phe Leu Arg Val Arg Ser Lys Arg Ser Arg Gly Gly
            340                 345                 350

His Ser Asp Tyr Met Asn Met Thr Pro Arg Arg Pro Gly Pro Thr Arg
        355                 360                 365

Lys His Tyr Gln Pro Tyr Ala Pro Pro Arg Asp Phe Ala Ala Tyr Arg
    370                 375                 380

Ser Lys Arg Gly Arg Lys Lys Leu Leu Tyr Ile Phe Lys Gln Pro Phe
385                 390                 395                 400
```

```
Met Arg Pro Val Gln Thr Thr Gln Glu Glu Asp Gly Cys Ser Cys Arg
            405                 410                 415

Phe Pro Glu Glu Glu Gly Gly Cys Glu Leu Lys Phe Ser Arg Ser
            420                 425                 430

Ala Asp Ala Pro Ala Tyr Gln Gln Gly Gln Asn Gln Leu Tyr Asn Glu
            435                 440                 445

Leu Asn Leu Gly Arg Arg Glu Glu Tyr Asp Val Leu Asp Lys Arg Arg
    450                 455                 460

Gly Arg Asp Pro Glu Met Gly Gly Lys Pro Gln Arg Arg Lys Asn Pro
465                 470                 475                 480

Gln Glu Gly Leu Tyr Asn Glu Leu Gln Lys Asp Lys Met Ala Glu Ala
                485                 490                 495

Tyr Ser Glu Ile Gly Met Lys Gly Glu Arg Arg Arg Gly Lys Gly His
            500                 505                 510

Asp Gly Leu Tyr Gln Gly Leu Ser Thr Ala Thr Lys Asp Thr Tyr Asp
            515                 520                 525

Ala Leu His Met Gln Ala Leu Pro Pro Arg
    530                 535

<210> SEQ ID NO 21
<211> LENGTH: 388
<212> TYPE: PRT
<213> ORGANISM: Unknown
<220> FEATURE:
<223> OTHER INFORMATION: HUMAN

<400> SEQUENCE: 21

Met Gly Trp Ser Cys Ile Ile Leu Phe Leu Val Ala Thr Ala Thr Gly
1               5                   10                  15

Val His Ser Asp Arg His Thr Val Phe Trp Asn Ser Ser Asn Pro Lys
                20                  25                  30

Phe Arg Asn Glu Asp Tyr Thr Ile His Val Gln Leu Asn Asp Tyr Val
            35                  40                  45

Asp Ile Ile Cys Pro His Tyr Glu Asp His Ser Val Ala Asp Ala Ala
    50                  55                  60

Met Glu Gln Tyr Ile Leu Tyr Leu Val Glu His Glu Glu Tyr Gln Leu
65                  70                  75                  80

Cys Gln Pro Gln Ser Lys Asp Gln Val Arg Trp Gln Cys Asn Arg Pro
                85                  90                  95

Ser Ala Lys His Gly Pro Glu Lys Leu Ser Glu Lys Phe Gln Arg Phe
            100                 105                 110

Thr Ala Phe Ala Leu Ala Lys Glu Phe Lys Ala Gly His Ser Tyr Tyr
        115                 120                 125

Tyr Ile Ser Lys Pro Ile His Gln His Glu Asp Arg Cys Leu Arg Leu
    130                 135                 140

Lys Val Thr Val Ser Gly Glu Gln Lys Leu Ile Ser Glu Glu Asp Leu
145                 150                 155                 160

Gly Gly Gly Pro Arg Lys Pro Thr Thr Thr Pro Ala Pro Arg Pro Pro
                165                 170                 175

Thr Pro Ala Pro Thr Ile Ala Ser Gln Pro Leu Ser Leu Arg Pro Glu
            180                 185                 190

Ala Cys Arg Pro Ala Ala Gly Gly Ala Val His Thr Arg Gly Leu Asp
        195                 200                 205

Phe Ala Cys Asp Ile Tyr Ile Trp Ala Pro Leu Ala Gly Thr Cys Gly
    210                 215                 220
```

```
Val Leu Leu Leu Ser Leu Val Ile Thr Lys Arg Gly Arg Lys Lys Leu
225                 230                 235                 240

Leu Tyr Ile Phe Lys Gln Pro Phe Met Arg Pro Val Gln Thr Thr Gln
            245                 250                 255

Glu Glu Asp Gly Cys Ser Cys Arg Phe Pro Glu Glu Glu Glu Gly Gly
        260                 265                 270

Cys Glu Leu Arg Val Lys Phe Ser Arg Ser Ala Asp Ala Pro Ala Tyr
        275                 280                 285

Gln Gln Gly Gln Asn Gln Leu Tyr Asn Glu Leu Asn Leu Gly Arg Arg
        290                 295                 300

Glu Glu Tyr Asp Val Leu Asp Lys Arg Arg Gly Arg Asp Pro Glu Met
305                 310                 315                 320

Gly Gly Lys Pro Gln Arg Arg Lys Asn Pro Gln Glu Gly Leu Tyr Asn
            325                 330                 335

Glu Leu Gln Lys Asp Lys Met Ala Glu Ala Tyr Ser Glu Ile Gly Met
            340                 345                 350

Lys Gly Glu Arg Arg Arg Gly Lys Gly His Asp Gly Leu Tyr Gln Gly
            355                 360                 365

Leu Ser Thr Ala Thr Lys Asp Thr Tyr Asp Ala Leu His Met Gln Ala
        370                 375                 380

Leu Pro Pro Arg
385

<210> SEQ ID NO 22
<211> LENGTH: 429
<212> TYPE: PRT
<213> ORGANISM: Unknown
<220> FEATURE:
<223> OTHER INFORMATION: HUMAN

<400> SEQUENCE: 22

Met Gly Trp Ser Cys Ile Ile Leu Phe Leu Val Ala Thr Ala Thr Gly
1               5                   10                  15

Val His Ser Asp Arg His Thr Val Phe Trp Asn Ser Ser Asn Pro Lys
            20                  25                  30

Phe Arg Asn Glu Asp Tyr Thr Ile His Val Gln Leu Asn Asp Tyr Val
        35                  40                  45

Asp Ile Ile Cys Pro His Tyr Glu Asp His Ser Val Ala Asp Ala Ala
    50                  55                  60

Met Glu Gln Tyr Ile Leu Tyr Leu Val Glu His Glu Glu Tyr Gln Leu
65                  70                  75                  80

Cys Gln Pro Gln Ser Lys Asp Gln Val Arg Trp Gln Cys Asn Arg Pro
                85                  90                  95

Ser Ala Lys His Gly Pro Glu Lys Leu Ser Glu Lys Phe Gln Arg Phe
            100                 105                 110

Thr Ala Phe Ala Leu Ala Lys Glu Phe Lys Ala Gly His Ser Tyr Tyr
        115                 120                 125

Tyr Ile Ser Lys Pro Ile His Gln His Glu Asp Arg Cys Leu Arg Leu
    130                 135                 140

Lys Val Thr Val Ser Gly Glu Gln Lys Leu Ile Ser Glu Glu Asp Leu
145                 150                 155                 160

Gly Gly Gly Pro Arg Lys Pro Thr Thr Thr Pro Ala Pro Arg Pro Pro
                165                 170                 175

Thr Pro Ala Pro Thr Ile Ala Ser Gln Pro Leu Ser Leu Arg Pro Glu
            180                 185                 190
```

```
Ala Cys Arg Pro Ala Ala Gly Gly Ala Val His Thr Arg Gly Leu Asp
            195                 200                 205

Phe Ala Cys Asp Ile Tyr Ile Trp Ala Pro Leu Ala Gly Thr Cys Gly
    210                 215                 220

Val Leu Leu Leu Ser Leu Val Ile Thr Arg Ser Lys Arg Ser Arg Gly
225                 230                 235                 240

Gly His Ser Asp Tyr Met Asn Met Thr Pro Arg Arg Pro Gly Pro Thr
                245                 250                 255

Arg Lys His Tyr Gln Pro Tyr Ala Pro Pro Arg Asp Phe Ala Ala Tyr
                260                 265                 270

Arg Ser Lys Arg Gly Arg Lys Lys Leu Leu Tyr Ile Phe Lys Gln Pro
                275                 280                 285

Phe Met Arg Pro Val Gln Thr Thr Gln Glu Glu Asp Gly Cys Ser Cys
    290                 295                 300

Arg Phe Pro Glu Glu Glu Glu Gly Gly Cys Glu Leu Arg Val Lys Phe
305                 310                 315                 320

Ser Arg Ser Ala Asp Ala Pro Ala Tyr Gln Gln Gly Gln Asn Gln Leu
                325                 330                 335

Tyr Asn Glu Leu Asn Leu Gly Arg Arg Glu Glu Tyr Asp Val Leu Asp
                340                 345                 350

Lys Arg Arg Gly Arg Asp Pro Glu Met Gly Gly Lys Pro Gln Arg Arg
                355                 360                 365

Lys Asn Pro Gln Glu Gly Leu Tyr Asn Glu Leu Gln Lys Asp Lys Met
                370                 375                 380

Ala Glu Ala Tyr Ser Glu Ile Gly Met Lys Gly Glu Arg Arg Arg Gly
385                 390                 395                 400

Lys Gly His Asp Gly Leu Tyr Gln Gly Leu Ser Thr Ala Thr Lys Asp
                405                 410                 415

Thr Tyr Asp Ala Leu His Met Gln Ala Leu Pro Pro Arg
                420                 425

<210> SEQ ID NO 23
<211> LENGTH: 351
<212> TYPE: PRT
<213> ORGANISM: Unknown
<220> FEATURE:
<223> OTHER INFORMATION: HUMAN

<400> SEQUENCE: 23

Met Gly Trp Ser Cys Ile Ile Leu Phe Leu Val Ala Thr Ala Thr Gly
1               5                   10                  15

Val His Ser Val Ser Asp Val Pro Arg Asp Leu Glu Val Val Ala Ala
                20                  25                  30

Thr Pro Thr Ser Leu Leu Ile Ser Trp Asp Ala Pro Ala Val Thr Val
                35                  40                  45

Arg Tyr Tyr Arg Ile Thr Tyr Gly Glu Thr Gly Gly Asn Ser Pro Val
                50                  55                  60

Gln Glu Phe Thr Val Pro Gly Ser Lys Ser Thr Ala Thr Ile Ser Gly
65                  70                  75                  80

Leu Lys Pro Gly Val Asp Tyr Thr Ile Thr Val Tyr Ala Val Thr Pro
                85                  90                  95

Arg Gly Asp Trp Asn Glu Gly Ser Lys Pro Ile Ser Ile Asn Tyr Arg
                100                 105                 110

Thr Glu Gln Lys Leu Ile Ser Glu Glu Asp Leu Gly Gly Gly Pro Arg
                115                 120                 125
```

Lys Pro Thr Thr Thr Pro Ala Pro Arg Pro Pro Thr Pro Ala Pro Thr
130                 135                 140

Ile Ala Ser Gln Pro Leu Ser Leu Arg Pro Glu Ala Cys Arg Pro Ala
145                 150                 155                 160

Ala Gly Gly Ala Val His Thr Arg Gly Leu Asp Phe Ala Cys Asp Ile
                165                 170                 175

Tyr Ile Trp Ala Pro Leu Ala Gly Thr Cys Gly Val Leu Leu Leu Ser
                180                 185                 190

Leu Val Ile Thr Lys Arg Gly Arg Lys Lys Leu Leu Tyr Ile Phe Lys
            195                 200                 205

Gln Pro Phe Met Arg Pro Val Gln Thr Thr Gln Glu Glu Asp Gly Cys
210                 215                 220

Ser Cys Arg Phe Pro Glu Glu Glu Gly Gly Cys Glu Leu Arg Val
225                 230                 235                 240

Lys Phe Ser Arg Ser Ala Asp Ala Pro Ala Tyr Gln Gln Gly Gln Asn
                245                 250                 255

Gln Leu Tyr Asn Glu Leu Asn Leu Gly Arg Arg Glu Glu Tyr Asp Val
            260                 265                 270

Leu Asp Lys Arg Arg Gly Arg Asp Pro Glu Met Gly Gly Lys Pro Gln
            275                 280                 285

Arg Arg Lys Asn Pro Gln Glu Gly Leu Tyr Asn Glu Leu Gln Lys Asp
290                 295                 300

Lys Met Ala Glu Ala Tyr Ser Glu Ile Gly Met Lys Gly Glu Arg Arg
305                 310                 315                 320

Arg Gly Lys Gly His Asp Gly Leu Tyr Gln Gly Leu Ser Thr Ala Thr
                325                 330                 335

Lys Asp Thr Tyr Asp Ala Leu His Met Gln Ala Leu Pro Pro Arg
            340                 345                 350

<210> SEQ ID NO 24
<211> LENGTH: 392
<212> TYPE: PRT
<213> ORGANISM: Unknown
<220> FEATURE:
<223> OTHER INFORMATION: HUMAN

<400> SEQUENCE: 24

Met Gly Trp Ser Cys Ile Ile Leu Phe Leu Val Ala Thr Ala Thr Gly
1               5                   10                  15

Val His Ser Val Ser Asp Val Pro Arg Asp Leu Glu Val Val Ala Ala
                20                  25                  30

Thr Pro Thr Ser Leu Leu Ile Ser Trp Asp Ala Pro Ala Val Thr Val
            35                  40                  45

Arg Tyr Tyr Arg Ile Thr Tyr Gly Glu Thr Gly Gly Asn Ser Pro Val
        50                  55                  60

Gln Glu Phe Thr Val Pro Gly Ser Lys Ser Thr Ala Thr Ile Ser Gly
65                  70                  75                  80

Leu Lys Pro Gly Val Asp Tyr Thr Ile Thr Val Tyr Ala Val Thr Pro
                85                  90                  95

Arg Gly Asp Trp Asn Glu Gly Ser Lys Pro Ile Ser Ile Asn Tyr Arg
                100                 105                 110

Thr Glu Gln Lys Leu Ile Ser Glu Glu Asp Leu Gly Gly Pro Arg
            115                 120                 125

Lys Pro Thr Thr Thr Pro Ala Pro Arg Pro Pro Thr Pro Ala Pro Thr
130                 135                 140

```
Ile Ala Ser Gln Pro Leu Ser Leu Arg Pro Glu Ala Cys Arg Pro Ala
145                 150                 155                 160

Ala Gly Gly Ala Val His Thr Arg Gly Leu Asp Phe Ala Cys Asp Ile
            165                 170                 175

Tyr Ile Trp Ala Pro Leu Ala Gly Thr Cys Gly Val Leu Leu Leu Ser
            180                 185                 190

Leu Val Ile Thr Arg Ser Lys Arg Ser Arg Gly Gly His Ser Asp Tyr
            195                 200                 205

Met Asn Met Thr Pro Arg Arg Pro Gly Pro Thr Arg Lys His Tyr Gln
210                 215                 220

Pro Tyr Ala Pro Pro Arg Asp Phe Ala Ala Tyr Arg Ser Lys Arg Gly
225                 230                 235                 240

Arg Lys Lys Leu Leu Tyr Ile Phe Lys Gln Pro Phe Met Arg Pro Val
                245                 250                 255

Gln Thr Thr Gln Glu Glu Asp Gly Cys Ser Cys Arg Phe Pro Glu Glu
                260                 265                 270

Glu Glu Gly Gly Cys Glu Leu Arg Val Lys Phe Ser Arg Ser Ala Asp
            275                 280                 285

Ala Pro Ala Tyr Gln Gln Gly Gln Asn Gln Leu Tyr Asn Glu Leu Asn
290                 295                 300

Leu Gly Arg Arg Glu Glu Tyr Asp Val Leu Asp Lys Arg Arg Gly Arg
305                 310                 315                 320

Asp Pro Glu Met Gly Gly Lys Pro Gln Arg Arg Lys Asn Pro Gln Glu
                325                 330                 335

Gly Leu Tyr Asn Glu Leu Gln Lys Asp Lys Met Ala Glu Ala Tyr Ser
            340                 345                 350

Glu Ile Gly Met Lys Gly Glu Arg Arg Arg Gly Lys Gly His Asp Gly
            355                 360                 365

Leu Tyr Gln Gly Leu Ser Thr Ala Thr Lys Asp Thr Tyr Asp Ala Leu
370                 375                 380

His Met Gln Ala Leu Pro Pro Arg
385                 390

<210> SEQ ID NO 25
<211> LENGTH: 665
<212> TYPE: PRT
<213> ORGANISM: Unknown
<220> FEATURE:
<223> OTHER INFORMATION: HUMAN

<400> SEQUENCE: 25

Met Gly Trp Ser Cys Ile Ile Leu Phe Leu Val Ala Thr Ala Thr Gly
1               5                   10                  15

Val His Ser Thr Ser Pro Cys Asp Asn Phe Asp Cys Gln Asn Gly Ala
            20                  25                  30

Gln Cys Ile Val Arg Ile Asn Glu Pro Ile Cys Gln Cys Leu Pro Gly
        35                  40                  45

Tyr Gln Gly Glu Lys Cys Glu Lys Leu Val Ser Val Asn Phe Ile Asn
50                  55                  60

Lys Glu Ser Tyr Leu Gln Ile Pro Ser Ala Lys Val Arg Pro Gln Thr
65                  70                  75                  80

Asn Ile Thr Leu Gln Ile Ala Thr Asp Glu Asp Ser Gly Ile Leu Leu
                85                  90                  95

Tyr Lys Gly Asp Lys Asp His Ile Ala Val Glu Leu Tyr Arg Gly Arg
            100                 105                 110
```

```
Val Arg Ala Ser Tyr Asp Thr Gly Ser His Pro Ala Ser Ala Ile Tyr
            115                 120                 125

Ser Val Glu Thr Ile Asn Asp Gly Asn Phe His Ile Val Glu Leu Leu
130                 135                 140

Ala Leu Asp Gln Ser Leu Ser Leu Ser Val Asp Gly Gly Asn Pro Lys
145                 150                 155                 160

Ile Ile Thr Asn Leu Ser Lys Gln Ser Thr Leu Asn Phe Asp Ser Pro
                165                 170                 175

Leu Tyr Val Gly Gly Met Pro Gly Lys Ser Asn Val Ala Ser Leu Arg
                180                 185                 190

Gln Ala Pro Gly Gln Asn Gly Thr Ser Phe His Gly Cys Ile Arg Asn
            195                 200                 205

Leu Tyr Ile Asn Ser Glu Leu Gln Asp Phe Gln Lys Val Pro Met Gln
            210                 215                 220

Thr Gly Ile Leu Pro Gly Cys Glu Pro Cys His Lys Lys Val Cys Ala
225                 230                 235                 240

His Gly Thr Cys Gln Pro Ser Ser Gln Ala Gly Phe Thr Cys Glu Cys
                245                 250                 255

Gln Glu Gly Trp Met Gly Pro Leu Cys Asp Gln Arg Thr Asn Asp Pro
            260                 265                 270

Cys Leu Gly Asn Lys Cys Val His Gly Thr Cys Leu Pro Ile Asn Ala
            275                 280                 285

Phe Ser Tyr Ser Cys Lys Cys Leu Glu Gly His Gly Gly Val Leu Cys
            290                 295                 300

Asp Glu Glu Glu Asp Leu Phe Asn Pro Cys Gln Ala Ile Lys Cys Lys
305                 310                 315                 320

His Gly Lys Cys Arg Leu Ser Gly Leu Gly Gln Pro Tyr Cys Glu Cys
                325                 330                 335

Ser Ser Gly Tyr Thr Gly Asp Ser Cys Asp Arg Glu Ile Ser Cys Arg
                340                 345                 350

Gly Glu Arg Ile Arg Asp Tyr Tyr Gln Lys Gln Gln Gly Tyr Ala Ala
            355                 360                 365

Cys Gln Thr Thr Lys Lys Val Ser Arg Leu Glu Cys Arg Gly Gly Cys
            370                 375                 380

Ala Gly Gly Gln Cys Cys Gly Pro Leu Arg Ser Lys Arg Arg Lys Tyr
385                 390                 395                 400

Ser Phe Glu Cys Thr Asp Gly Ser Ser Phe Val Asp Glu Val Glu Lys
                405                 410                 415

Val Val Lys Cys Gly Cys Thr Arg Cys Val Ser Glu Gln Lys Leu Ile
            420                 425                 430

Ser Glu Glu Asp Leu Gly Gly Gly Pro Arg Lys Pro Thr Thr Thr Pro
            435                 440                 445

Ala Pro Arg Pro Pro Thr Pro Ala Pro Thr Ile Ala Ser Gln Pro Leu
450                 455                 460

Ser Leu Arg Pro Glu Ala Cys Arg Pro Ala Ala Gly Gly Ala Val His
465                 470                 475                 480

Thr Arg Gly Leu Asp Phe Ala Cys Asp Ile Tyr Ile Trp Ala Pro Leu
                485                 490                 495

Ala Gly Thr Cys Gly Val Leu Leu Ser Leu Val Ile Thr Lys Arg
                500                 505                 510

Gly Arg Lys Lys Leu Leu Tyr Ile Phe Lys Gln Pro Phe Met Arg Pro
            515                 520                 525
```

```
Val Gln Thr Thr Gln Glu Glu Asp Gly Cys Ser Cys Arg Phe Pro Glu
            530                 535                 540

Glu Glu Glu Gly Gly Cys Glu Leu Arg Val Lys Phe Ser Arg Ser Ala
545                 550                 555                 560

Asp Ala Pro Ala Tyr Gln Gln Gly Gln Asn Gln Leu Tyr Asn Glu Leu
                565                 570                 575

Asn Leu Gly Arg Arg Glu Glu Tyr Asp Val Leu Asp Lys Arg Arg Gly
            580                 585                 590

Arg Asp Pro Glu Met Gly Gly Lys Pro Gln Arg Arg Lys Asn Pro Gln
            595                 600                 605

Glu Gly Leu Tyr Asn Glu Leu Gln Lys Asp Lys Met Ala Glu Ala Tyr
610                 615                 620

Ser Glu Ile Gly Met Lys Gly Glu Arg Arg Gly Lys Gly His Asp
625                 630                 635                 640

Gly Leu Tyr Gln Gly Leu Ser Thr Ala Thr Lys Asp Thr Tyr Asp Ala
                645                 650                 655

Leu His Met Gln Ala Leu Pro Pro Arg
            660                 665

<210> SEQ ID NO 26
<211> LENGTH: 706
<212> TYPE: PRT
<213> ORGANISM: Unknown
<220> FEATURE:
<223> OTHER INFORMATION: HUMAN

<400> SEQUENCE: 26

Met Gly Trp Ser Cys Ile Ile Leu Phe Leu Val Ala Thr Ala Thr Gly
1               5                   10                  15

Val His Ser Thr Ser Pro Cys Asp Asn Phe Asp Cys Gln Asn Gly Ala
                20                  25                  30

Gln Cys Ile Val Arg Ile Asn Glu Pro Ile Cys Gln Cys Leu Pro Gly
            35                  40                  45

Tyr Gln Gly Glu Lys Cys Glu Lys Leu Val Ser Val Asn Phe Ile Asn
50                  55                  60

Lys Glu Ser Tyr Leu Gln Ile Pro Ser Ala Lys Val Arg Pro Gln Thr
65                  70                  75                  80

Asn Ile Thr Leu Gln Ile Ala Thr Asp Glu Asp Ser Gly Ile Leu Leu
                85                  90                  95

Tyr Lys Gly Asp Lys Asp His Ile Ala Val Glu Leu Tyr Arg Gly Arg
                100                 105                 110

Val Arg Ala Ser Tyr Asp Thr Gly Ser His Pro Ala Ser Ala Ile Tyr
            115                 120                 125

Ser Val Glu Thr Ile Asn Asp Gly Asn Phe His Ile Val Glu Leu Leu
130                 135                 140

Ala Leu Asp Gln Ser Leu Ser Leu Ser Val Asp Gly Gly Asn Pro Lys
145                 150                 155                 160

Ile Ile Thr Asn Leu Ser Lys Gln Ser Thr Leu Asn Phe Asp Ser Pro
                165                 170                 175

Leu Tyr Val Gly Gly Met Pro Gly Lys Ser Asn Val Ala Ser Leu Arg
            180                 185                 190

Gln Ala Pro Gly Gln Asn Gly Thr Ser Phe His Gly Cys Ile Arg Asn
        195                 200                 205

Leu Tyr Ile Asn Ser Glu Leu Gln Asp Phe Gln Lys Val Pro Met Gln
210                 215                 220
```

-continued

```
Thr Gly Ile Leu Pro Gly Cys Glu Pro Cys His Lys Val Cys Ala
225                 230                 235                 240

His Gly Thr Cys Gln Pro Ser Ser Gln Ala Gly Phe Thr Cys Glu Cys
            245                 250                 255

Gln Glu Gly Trp Met Gly Pro Leu Cys Asp Gln Arg Thr Asn Asp Pro
        260                 265                 270

Cys Leu Gly Asn Lys Cys Val His Gly Thr Cys Leu Pro Ile Asn Ala
    275                 280                 285

Phe Ser Tyr Ser Cys Lys Cys Leu Glu Gly His Gly Gly Val Leu Cys
290                 295                 300

Asp Glu Glu Asp Leu Phe Asn Pro Cys Gln Ala Ile Lys Cys Lys
305                 310                 315                 320

His Gly Lys Cys Arg Leu Ser Gly Leu Gly Gln Pro Tyr Cys Glu Cys
            325                 330                 335

Ser Ser Gly Tyr Thr Gly Asp Ser Cys Asp Arg Glu Ile Ser Cys Arg
        340                 345                 350

Gly Glu Arg Ile Arg Asp Tyr Tyr Gln Lys Gln Gly Tyr Ala Ala
    355                 360                 365

Cys Gln Thr Thr Lys Lys Val Ser Arg Leu Glu Cys Arg Gly Gly Cys
370                 375                 380

Ala Gly Gly Gln Cys Cys Gly Pro Leu Arg Ser Lys Arg Arg Lys Tyr
385                 390                 395                 400

Ser Phe Glu Cys Thr Asp Gly Ser Ser Phe Val Asp Glu Val Glu Lys
            405                 410                 415

Val Val Lys Cys Gly Cys Thr Arg Cys Val Ser Glu Gln Lys Leu Ile
        420                 425                 430

Ser Glu Glu Asp Leu Gly Gly Pro Arg Lys Pro Thr Thr Thr Pro
    435                 440                 445

Ala Pro Arg Pro Pro Thr Pro Ala Pro Thr Ile Ala Ser Gln Pro Leu
450                 455                 460

Ser Leu Arg Pro Glu Ala Cys Arg Pro Ala Ala Gly Gly Ala Val His
465                 470                 475                 480

Thr Arg Gly Leu Asp Phe Ala Cys Asp Ile Tyr Ile Trp Ala Pro Leu
            485                 490                 495

Ala Gly Thr Cys Gly Val Leu Leu Leu Ser Leu Val Ile Thr Arg Ser
        500                 505                 510

Lys Arg Ser Arg Gly Gly His Ser Asp Tyr Met Asn Met Thr Pro Arg
    515                 520                 525

Arg Pro Gly Pro Thr Arg Lys His Tyr Gln Pro Tyr Ala Pro Pro Arg
530                 535                 540

Asp Phe Ala Ala Tyr Arg Ser Lys Arg Gly Arg Lys Lys Leu Leu Tyr
545                 550                 555                 560

Ile Phe Lys Gln Pro Phe Met Arg Pro Val Gln Thr Thr Gln Glu Glu
            565                 570                 575

Asp Gly Cys Ser Cys Arg Phe Pro Glu Glu Glu Gly Gly Cys Glu
        580                 585                 590

Leu Arg Val Lys Phe Ser Arg Ser Ala Asp Ala Pro Ala Tyr Gln Gln
    595                 600                 605

Gly Gln Asn Gln Leu Tyr Asn Glu Leu Asn Leu Gly Arg Arg Glu Glu
610                 615                 620

Tyr Asp Val Leu Asp Lys Arg Gly Arg Asp Pro Glu Met Gly Gly
625                 630                 635                 640

Lys Pro Gln Arg Arg Lys Asn Pro Gln Glu Gly Leu Tyr Asn Glu Leu
```

```
                    645                 650                 655
Gln Lys Asp Lys Met Ala Glu Ala Tyr Ser Glu Ile Gly Met Lys Gly
            660                 665                 670

Glu Arg Arg Arg Gly Lys Gly His Asp Gly Leu Tyr Gln Gly Leu Ser
            675                 680                 685

Thr Ala Thr Lys Asp Thr Tyr Asp Ala Leu His Met Gln Ala Leu Pro
    690                 695                 700

Pro Arg
705

<210> SEQ ID NO 27
<211> LENGTH: 41
<212> TYPE: PRT
<213> ORGANISM: Unknown
<220> FEATURE:
<223> OTHER INFORMATION: HUMAN

<400> SEQUENCE: 27

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```